(12) United States Patent
Lee et al.

(10) Patent No.: US 12,333,413 B1
(45) Date of Patent: Jun. 17, 2025

(54) APPARATUS AND METHOD FOR TRAINING AN ARTIFICIAL INTELLIGENCE-SUPPORTED DIAGNOSTIC ASSESSMENT TOOL

(71) Applicant: Mayo Foundation for Medical Education and Research, Rochester, MN (US)

(72) Inventors: Eunjung Lee, Rochester, MN (US); Francisco Lopez-Jimenez, Rochester, MN (US); Paul A. Friedman, Rochester, MN (US); Itzhak Zachi Attia, Rochester, MN (US); Jae K. Oh, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 0 days.

(21) Appl. No.: 18/592,680

(22) Filed: Mar. 1, 2024

(51) Int. Cl.
| | | |
|---|---|---|
| *A61B 5/349* | (2021.01) | |
| *A61B 8/08* | (2006.01) | |
| *G06N 3/0464* | (2023.01) | |
| *G16H 50/20* | (2018.01) | |
| *G16H 30/40* | (2018.01) | |

(52) U.S. Cl.
CPC .......... *G06N 3/0464* (2023.01); *A61B 5/349* (2021.01); *A61B 8/0883* (2013.01); *G16H 50/20* (2018.01); *G16H 30/40* (2018.01)

(58) Field of Classification Search
CPC ...................................................... A61B 5/346
See application file for complete search history.

(56) References Cited

U.S. PATENT DOCUMENTS

| | | |
|---|---|---|
| 11,445,918 B2 | 9/2022 | Peterson |
| 11,589,829 B2 | 2/2023 | Khosousi et al. |

(Continued)

FOREIGN PATENT DOCUMENTS

| | | | |
|---|---|---|---|
| WO | 2023230345 A1 | | 11/2023 |
| WO | WO 2023/230345 | * | 11/2023 |

OTHER PUBLICATIONS

Chen et al., "Artificial Intelligence-Enable Electrocardiogramtricular Dysfunction and Future Cardiovascular Outcomes: A Retrospective Analysis", Mar. 2022, Journal of Personalized Medicine (Year: 2022).*

(Continued)

*Primary Examiner* — George R Evanisko
(74) *Attorney, Agent, or Firm* — Caldwell Intellectual Property Law

(57) ABSTRACT

An apparatus and method for training an artificial intelligence-supported diagnostic assessment tool may provide rapid and accurate prognosis determinations. Apparatus may include at least a processor configured to receive a plurality of multi-channel sensor readings of physiological data, generate training data correlating each of the plurality of multi-channel sensor readings with a plurality of diagnostic labels, train a neural network using the plurality of diagnostic labels, receive a time series input describing user physiological data from at least a sensor, input the time series input into the trained neural network, generate diagnostic data as a function of the time series input and the trained neural network, determine prognostic data as a function of the diagnostic data, and output the prognostic data.

16 Claims, 24 Drawing Sheets

(56) References Cited

U.S. PATENT DOCUMENTS

| | | | |
|---|---|---|---|
| 11,657,921 | B2 | 5/2023 | Zimmerman et al. |
| 2020/0397313 | A1 | 12/2020 | Attia et al. |
| 2022/0000041 | A1 | 1/2022 | Baram |
| 2022/0189634 | A1 | 6/2022 | Wagner et al. |
| 2022/0189636 | A1 | 6/2022 | Wagner et al. |
| 2023/0309967 | A1 | 10/2023 | Vaid et al. |
| 2023/0395248 | A1 | 12/2023 | Sipe et al. |

OTHER PUBLICATIONS

Kashou et al.; Artificial intelligence—augmented electrocardiogram detection of left ventricular systolic dysfunction in the general population; Mayo Clinic proceedings, vol. 96, No. 10, pp. 2576-2586; Oct. 1, 2021; Retrieved at https://www.ncbi.nlm.nih.gov/pmc/articles/PMC9904428/.

Chen et al.; Artificial intelligence-enabled electrocardiogramtricular dysfunction and future cardiovascular outcomes: a retrospective analysis; Journal of Personalized Medicine 12, No. 3: 455; Mar. 13, 2022; Retrieved at https://www.mdpi.com/2075-4426/12/3/455.

Huang et al.; Artificial intelligence-enabled electrocardiogrameening for left ventricular systolic dysfunction and mortality risk prediction; Frontiers in Cardiovascular Medicine 10: 1070641; Mar. 3, 2023; Retrieved at https://www.frontiersin.org/articles/10.3389/fcvm.2023.1070641/full.

Bjerken et al.; Artificial intelligence enabled ECG screening for left ventricular systolic dysfunction: a systematic review; Heart Failure Reviews 28, No. 2: 419-430; Nov. 8, 2022; Retrieved at https://link.springer.com/article/10.1007/s10741-022-10283-1.

Naz et al., From ECG signals to images: a transformation based approach for deep learning, (journal), Feb. 10, 2021, PeerJ Computer Science, 7: e386, National Library of Medicine.

* cited by examiner

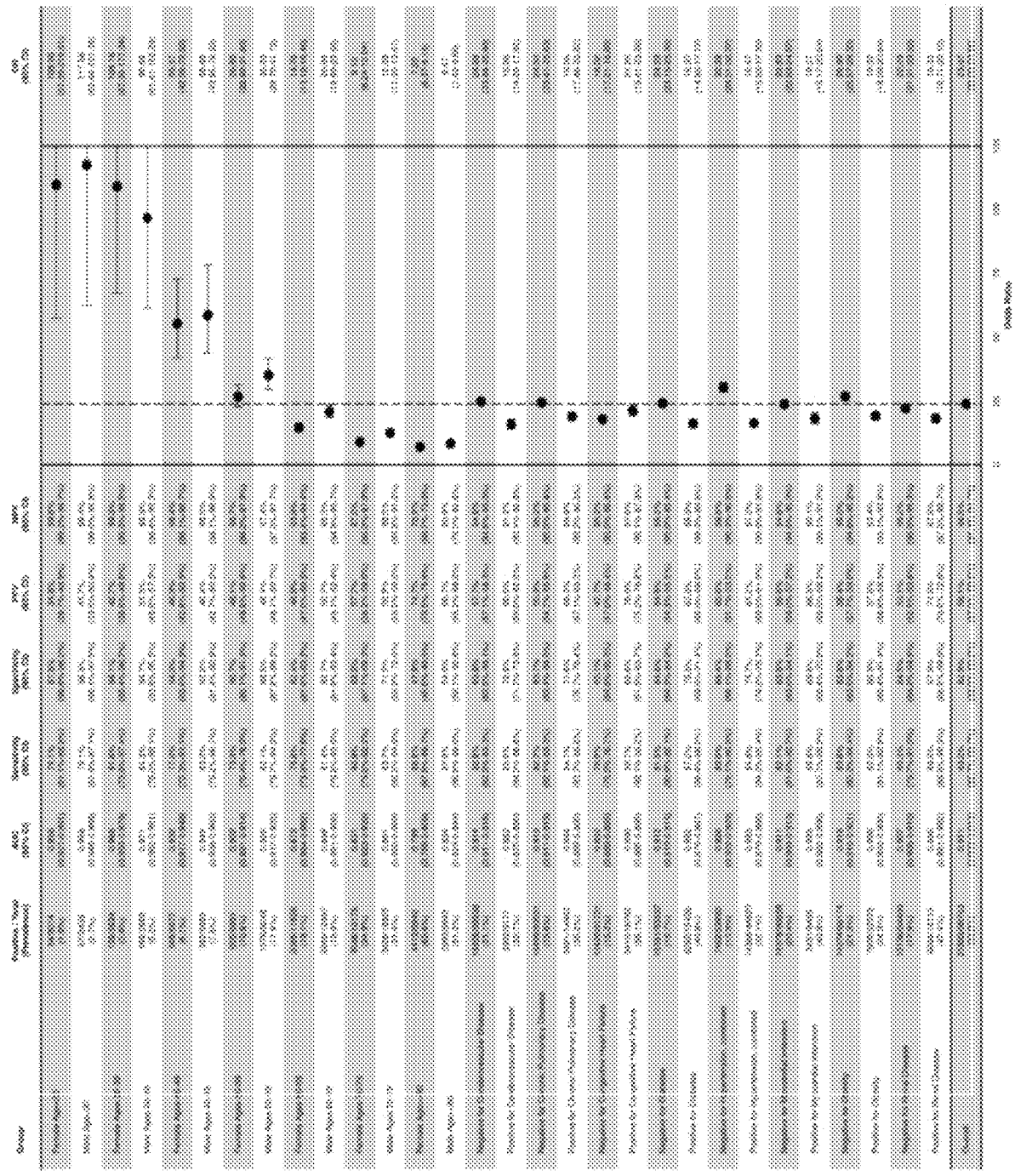
FIG. 5F2

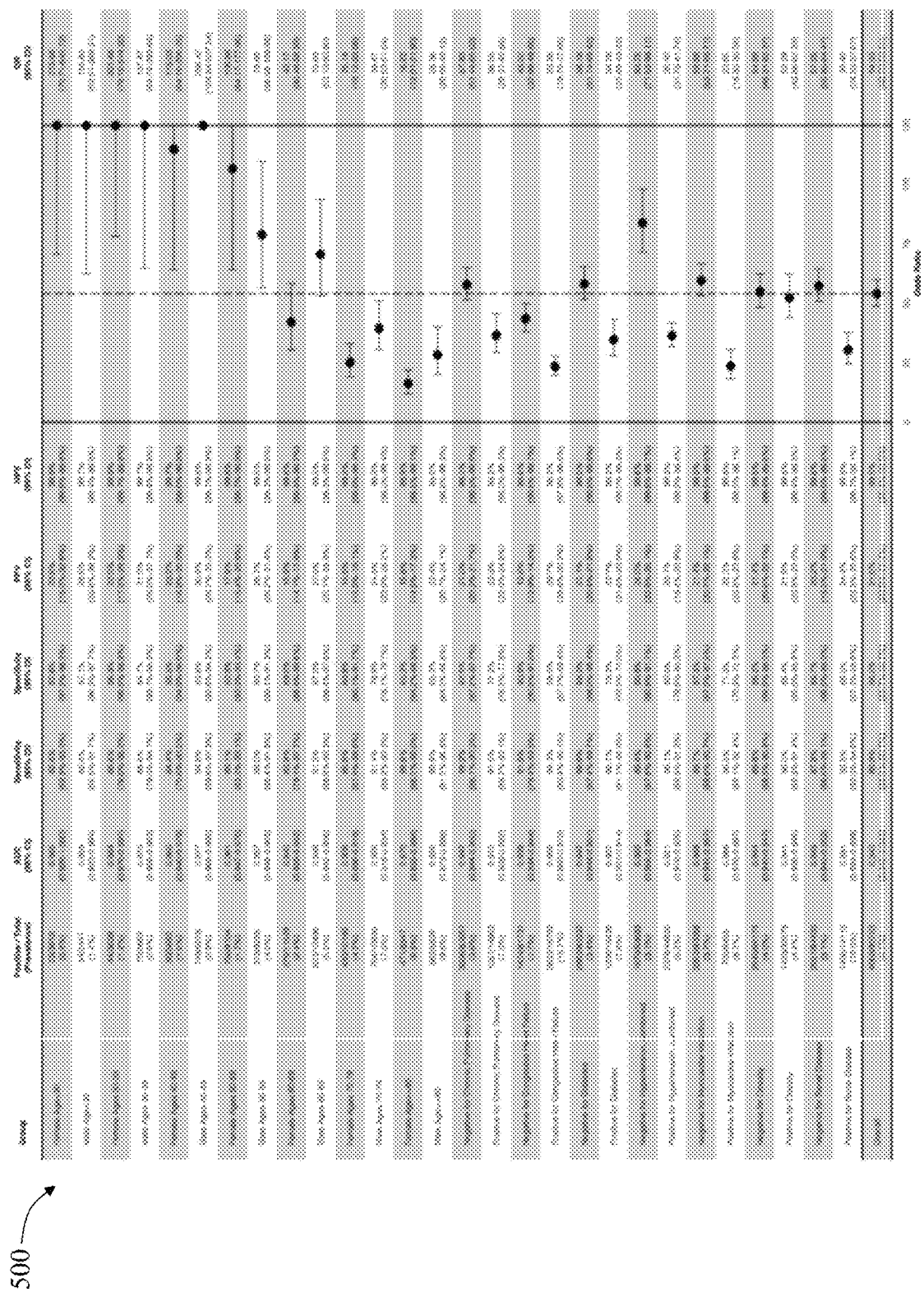
FIG. 5F3

APPARATUS AND METHOD FOR TRAINING AN ARTIFICIAL INTELLIGENCE-SUPPORTED DIAGNOSTIC ASSESSMENT TOOL

FIELD OF THE INVENTION

The present invention generally relates to the field of medical diagnosis. In particular, the present invention is directed to an apparatus and method for training an artificial intelligence-supported diagnostic assessment tool.

BACKGROUND

Assessment of left ventricular (LV) systolic and diastolic dysfunction (LVSD and LVDD respectively) is essential for the evaluation and management of cardiac disease. Generally, patients undergo echocardiograms, which can be laborious, expensive, not readily available and sometimes inaccurate if performed incorrectly. A rapid, easily performed test to assess both LVSD and LVDD in order to identify potential cardiac disease is lacking.

SUMMARY OF THE DISCLOSURE

In an aspect, an apparatus and method for training an artificial intelligence-supported diagnostic assessment tool may provide rapid and accurate prognosis determinations. Apparatus may include at least a processor configured to receive a plurality of multi-channel sensor readings of physiological data, generate training data correlating each of the plurality of multi-channel sensor readings with a plurality of diagnostic labels, train a neural network using the plurality of diagnostic labels, receive a time series input describing user physiological data from at least a sensor, input the time series input into the trained neural network, generate diagnostic data as a function of the time series input and the trained neural network, determine prognostic data as a function of the diagnostic data, and output the prognostic data. In another aspect, apparatus for artificial intelligence-supported diagnostic assessment may provide predictive diagnostic data based solely on electrocardiogram data at the same level of accuracy as an echocardiogram.

These and other aspects and features of non-limiting embodiments of the present invention will become apparent to those skilled in the art upon review of the following description of specific non-limiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein.

The drawings are not necessarily to scale and may be illustrated by phantom lines, diagrammatic representations and fragmentary views. In certain instances, details that are not necessary for an understanding of the embodiments or that render other details difficult to perceive may have been omitted.

DETAILED DESCRIPTION

At a high level, aspects of the present disclosure are directed to apparatuses and methods of training an artificial intelligence-supported diagnostic assessment tool. Apparatus may include at least a processor configured to receive a plurality of multi-channel sensor readings of physiological data, generate training data correlating each of the plurality of multi-channel sensor readings with a plurality of diagnostic labels, train a neural network using the plurality of diagnostic labels, receive a time series input describing user physiological data from at least a sensor, input the time series input into the trained neural network, generate diagnostic data as a function of the time series input and the trained neural network, determine prognostic data as a function of the diagnostic data, and output the prognostic data. Aspects of the present disclosure can be used to evaluate and manage medical diseases rapidly, accurately, and cost-effectively. Aspects of the present disclosure can also be used to predict future prognosis. This is so, at least in part, because the diagnostic tool is aided by AI and allows for a generative prediction model to grow and adapt. Exemplary embodiments illustrating aspects of the present disclosure are described below in the context of several specific examples.

Figure 1:
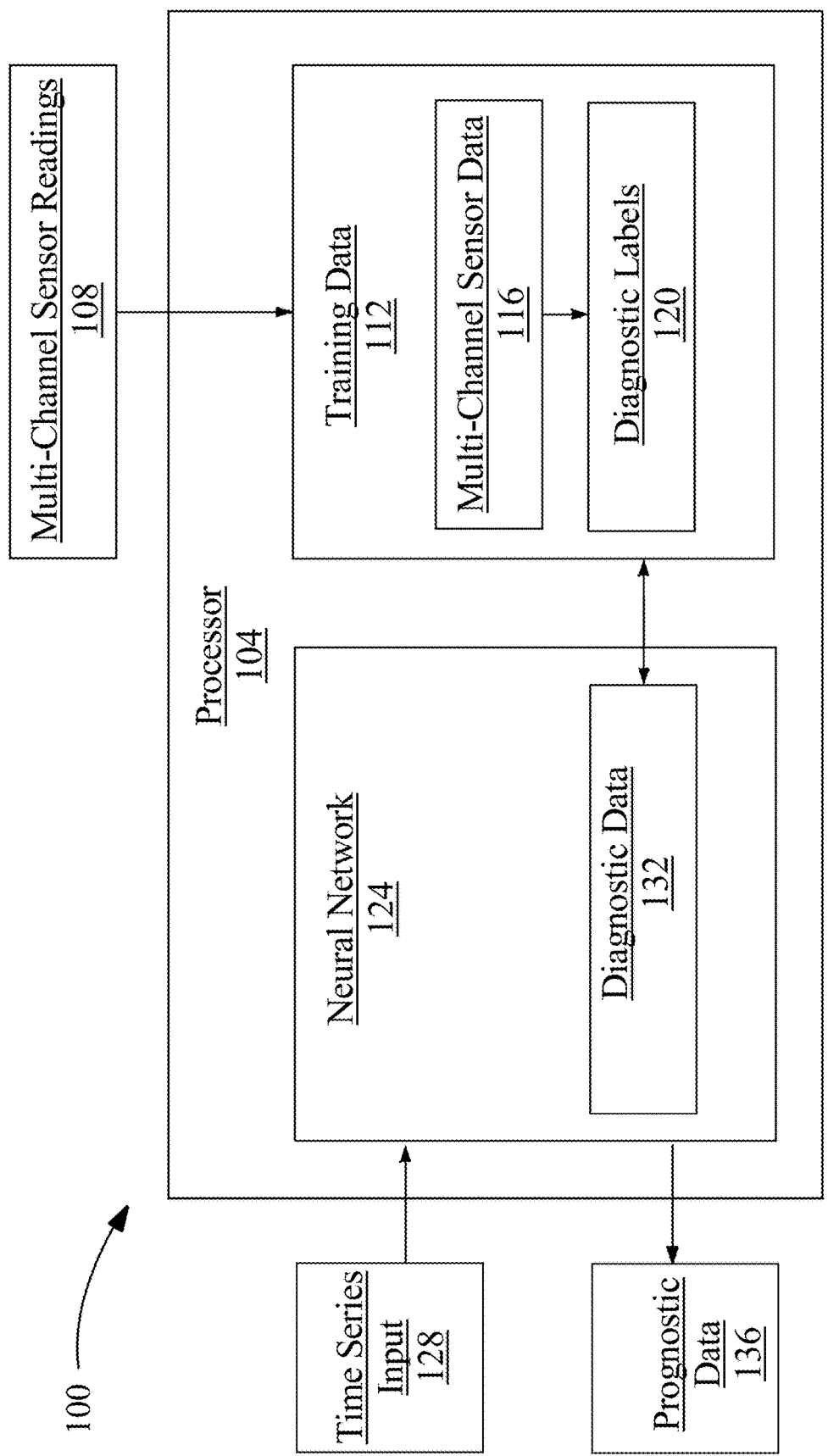
FIG. 1 illustrates a system block diagram of an apparatus for artificial intelligence-supported diagnostic assessments.

Referring now to FIG. 1, an exemplary embodiment of an apparatus for artificial intelligence-supported diagnostic assessments 100 is illustrated. In an embodiment, apparatus 100 includes at least a processor 104, wherein processor 104 is configured to receive a plurality of multi-channel sensor readings 108 of physiological data, generate training data 112 correlating each of the plurality of multi-channel sensor readings 108 with a plurality of diagnostic labels 120, train a neural network 124 using the plurality of diagnostic labels 120 and multi-channel sensor data 116, receive a time series input 128 describing user physiological data from at least a sensor, input the time series input 128 into the trained neural network 124, generate diagnostic data 132 as a function of the time series input 128 and the trained neural network 124, determine prognostic data 136 as a function of the diagnostic data 132, and output the prognostic data 136. "Diagnostic labels," as used throughout this disclosure are closely related to diagnostic data 132 and classify data related to diagnosis of a patient. For example, and without limitation a diagnostic label may include, left ventricle ejection fraction (LVEF) data, probability of left ventricle diastolic dysfunction (LVDD), LVDD within a certain time frame, and/or the like. Alternatively, and without limitation, a diagnostic label may be binary (e.g. yes/no or true/false), binary labels may indicate a risk above a certain threshold. As used throughout this disclosure, a "time series input" is a type of data that represents a sequence of observations or measurements recorded at specific time intervals. In a time series, each data point is associated with a particular timestamp, and the data is collected and organized in chronological order. "Diagnostic data," as used in this disclosure, is data associated with the diagnosis of a users' medical condition and/or health issue. Furthermore, as used in this disclosure, "prognostic data" is data associated with predictions about the future health of a user. With continued reference to FIG. 1, a plurality of multi-channel sensor readings 108 of physiological data may include sensor readings from one or more diagnostic tools, such as without limitation an echocardiogram, an electrocardiogram (ECG), and/or an electroencephalogram (EEG). A "channel," as used in this disclosure, is a distinct medium, mechanism, and/or pathway by which a signal can travel. Two distinct channels may include, for instance, two distinct data paths for signals, such as two signals received from and/or via two sensors or leads, signals received via two distinct wires, signals received by two distinct antenna, two distinct frequency ranges such as corresponding to two distinct passbands in radiofrequency communication, two distinct "tracks" in an audio or other data recording, or the like. The plurality of multi-channel sensor readings 108 may be correlated to one another in a way that pairs a distinct multi-channel sensor reading with another distinct multi-channel sensor reading. These correlations may be an embodiment of multi-channel sensor data 116. Additionally, multi-channel sensor readings 108 may individually be embodiments of multi-sensor data 116. For example, and without limitation, an ECG reading may generate ECG data and may be paired with an echocardiogram reading that generates echocardiogram data. This may allow for the generation of training data 112 that associates specific ECG data with specific echocardiogram data. Additional multi-channel sensor readings 108 may include synthetic generation of echocardiogram data from ECG data. This may be implemented, without limitation, as disclosed in U.S. application Ser. No. 18/517,640, filed on Nov. 22, 2023 and entitled "SYSTEM AND METHOD FOR GENERATING ECHOCARDIOGRAM INFORMATION FROM ELECTROCARDIOGRAM" the entirety of which is incorporated herein by reference. Furthermore, a correlation may be made between similar types of multi-channel sensor readings 108 with mismatched-channel configurations. Physiological data may include electrical signals of the body, heart rate, blood glucose, blood pressure, respiration rate, body temperature, and/or the like.

Continuing to reference FIG. 1, generating training data 112 correlating each of the plurality of multi-channel sensor readings 108 with a plurality of diagnostic labels 120 may be implemented without limitation, as disclosed in U.S. application Ser. No. 17/552,246, filed on Dec. 15, 2021 and entitled "SYSTEMS AND METHODS FOR DIAGNOSING A HEALTH CONDITION BASED ON PATIENT TIME SERIES DATA" the entirety of which is incorporated herein by reference. Additionally, generation of training data 112 may be implemented, without limitation, as disclosed in U.S. application Ser. No. 17/500,287, filed on Oct. 13, 2021 and entitled "NONINVASIVE METHODS FOR DETECTION OF PULMONARY HYPERTENSION" the entirety of which is incorporated herein by reference. This may be further implemented, without limitation, as disclosed in U.S. application Ser. No. 16/754,007, filed on Apr. 6, 2020 and entitled "ECG-BASED CARDIAC EJECTION-FRACTION SCREENING" the entirety of which is incorporated herein by reference.

With continued reference to FIG. 1, in an embodiment, neural network 124, may include a multi-output convolutional neural network (CNN). CNNs are especially useful for computer vision tasks, such as image recognition and classification because they are designed to learn the spatial hierarchies of features by capturing essential features in early layers and complex patterns in deeper layers. Therefore, a multi-output CNN is a predictive model that simultaneously outputs a set of two or more labels that measure different concepts. Ultimately, two or more separate, although related, classification problems are solved concurrently within the same model. For example, and without limitation, neural network 124 may be trained using exemplary inputs such as, 12-lead ECG data performed within 14 days of a transthoracic echocardiography, echocardiography data, multi-channel sensor reading data, diagnostic labels 120, diagnostic data 132, and/or the like and correlated to exemplary outputs, such as diagnostic data 132, including ejection fraction percentages, filling pressure, and the like, as well as diagnoses of normal LV, LVSD, LVDD, prognostic data 136, diagnostic data 132, and/or the like. Training data 112 may include any training data 112 as discussed and/or incorporated herein. Training data 112 may be used reiteratively, where outputs are used as new and additional training data 112. Training of network 124 may occur at apparatus 100 and/or remotely. Likewise, retraining of network 124 may occur at apparatus 100 and/or remotely. Network 124 may additionally be trained on various other channel variations, including without limitation, 6-lead ECG and/or other time series input diagnostic tools. Additional nonlimiting examples of neural network 124 may include recurrent neural networks (RNN), Multi-Layer Perceptron (PLP), and/or the like. Neural network 124 may include any model as discussed throughout this disclosure. Neural network 124 may be trained on general-use lead data, and/or alternatively on reduced general-use lead data. "General-use" refers to the typical lead count used for any given diagnostic tool. For example, and without limitation, ECGs typically use 12-lead ECG data. Likewise, general-use in EEGs may require up to 64 or more electrodes or leads in a 10-20 lead placement. Reduced general-use lead data therefore refers to a reduction in the electrodes and/or leads used in acquiring the lead data.

In further reference to FIG. 1, receiving a time series input 128 describing user physiological data from at least a sensor may include receiving data manually input by a user. Manual input may include data in any form or embodiment of time series input 128 as discussed throughout this disclosure. Alternatively, receiving a time series input 128 may include receiving data output from another machine learning model. For example, and without limitation, receiving a time series input 128 may include an output from machine learning model configured to generate determinations using mismatched-channel signals. This embodiment may allow for the use of a diagnostic tool with a first set of signals using a number of channels to output a converted signal set in a target configuration that is either higher or lower than the first set of signals using a number of channels and used within time series input 128. This configuration may aid in the ease and cost of assessment as not all embodiments of diagnostic tests will be in the same channel configuration. Outputs of an additional machine learning model used as time series input 128 may include data in any form or embodiment as discussed throughout this disclosure. A "sensor," as used in this disclosure is any embodiment capable of detecting a phenomenon. For example, and without limitation an electrode may be able to detect or sense the electrical activity of the heart and/or brain. The sensor may be communicatively connected to apparatus 100 and/or sensor information may be entered manually by user interaction. Furthermore, sensor may exist apart from apparatus 100 but maintain its connection through communication with apparatus 100 that may be physical and/or through a remote device. A specific, non-limiting exemplary embodiment of a time series input 128 may include "array ([[24, 29, 5, . . . , 20, 15, 24], [20, 10, −10, . . . , 20, 20, 20], [20, 10, −10, . . . , 44, 39, 39], . . . , [20, 39, 19, . . . , 10, 24, 10], [24, 29, 5, . . . , 10, 20, 5], [20, 5, −15, . . . , −5, 15, 5]], dtype=int16)."

Continuing to reference FIG. 1, in an embodiment, time series input 128 may include electrocardiogram (ECG) data. An ECG is a medical method of monitoring the activity, speed, and/or rhythm of the heart. ECG is used as a test to diagnose pathologies of the heart such as cardiac arrhythmias, atrial and ventricular hypertrophy, conduction disorders, injury or necrosis of the myocardium, myocardial infarction, ischemic heart disease, electrolyte disorders, lesions in the myocardium, and some drug toxicity diagnoses. Assessing diastolic function (DF) and filling pressure (FP) are key components in the diagnosis and management of heart failure with preserved ejection fraction (HFpEF). However, a rapid and easily performed test to assess these components is lacking. Therefore, in an embodiment, apparatus 100 enables the AI-assisted assessment of these key components through the use of ECG data. Diastolic function may further be described in terms of systolic and/or diastolic dysfunction. Assessment may focus particularly on the left ventricular (LV) and may require assessment of LV systolic dysfunction (LVSD) and/or LV diastolic dysfunction (LVDD) for the evaluation and management of cardiac disease. "Systolic," relates to the phase of the heartbeat when the heart muscle contracts and pumps blood from the chambers of the heart into the arteries of the body. Alternately, "diastolic" relates to the phase of the heartbeat when the heart muscle relaxes and allows the chambers of the heart to fill with blood. "Dysfunction" generally relates to an abnormality or impairment in the function of a specific bodily organ or system, for example an abnormality of the heartbeat rhythm. HFpEF is a clinical syndrome in which patients have clinical features of heart failure in the presence of normal or near-normal left ventricular ejection fraction, usually defined as ejection fraction at 50% or above. HFpEF is not a single condition but a result of many different pathologies, adding challenges to management. However, a common diagnostic finding is increased diastolic filling pressure. As management of HFpEF, especially in later stages, is difficult, prevention and early recognition and diagnosis are key in battling the disease. Diagnosis of HFpEF generally may rely on a variety of factors drawn from the interpretation of a full echocardiogram, such as without limitation, LF mass, left atrial volume and assessment of diastolic function. An "echocardiogram" is a test of the action of the heart using ultrasound waves to produce a visual display, used for the diagnosis or monitoring of heart disease. Additionally, there are two forms of echocardiogram: transthoracic and/or transesophageal. A transthoracic echocardiogram is a test that uses ultrasound and its probe outside of the chest to create images of your heart and is the most common type of echocardiogram as it is less invasive than its counterpart. Transesophageal echocardiogram, however, is invasive, as the test requires an endoscope to introduce an ultrasound probe down a patient's esophagus.

With continued reference to FIG. 1, apparatus 100 may operate as a predictive model able to determine diagnosis based on LV function alone, obtained through ECG. Time series input 128 may include 12-lead ECG data. Alternatively, time series input 128 may include 6-lead ECG data, for example, data may be procured from an AliveCor 6-lead ECG. The use of the "12" indicates the capturing of electrical activity of a patient's heart from 12 different perspectives being measured. Likewise, a 6-lead ECG would indicate 6 different perspectives being measured. "Lead," as used in this disclosure is one or more electrodes attached to the skin to detect a heart's electric signals. As used in this disclosure, "ECG data" refers to the electrical signal recorded from a user's heart by placing electrodes on the user's body. The signals of a users' heart are shown as waves, which may then be read to indicate potential and current issues with the rhythm and/or function of their heart, which may further implicate certain medical diagnoses.

Continuing to reference FIG. 1, in an embodiment, processor 104 may generate diagnostic data 132 as a function of the time series input 128 and the trained neural network 124. Furthermore, diagnostic data 132 may identify a condition of the user based on the time series data by determining prognostic data 136 as a function of the diagnostic data 132. Identification may include an assessment of normal LV, LVSD, LVDD, or both LVSD and LVDD. LVSD, for purposes of this disclosure, is defined as LV ejection fraction (EF) less than 50%. "Ejection fraction" refers to the measurement of the percentage of blood leaving the heart each time it contracts. Likewise, LVDD is defined as increased LV filling pressure (FP). FP is considered elevated or increased when the mean pulmonary capillary wedge pressure (PCWP) is greater than 15 mm Hg or when the LV end-diastolic pressure (LVEDP) is greater than 16 mm Hg. Diagnostic data 132 may be used to classify the user into a plurality of groups. The plurality of groups may include normal LV function, LVSD only, LVDD only, and/or both LVSD and LVDD.

Further referencing FIG. 1, processor 104 may be configured to determine prognostic data 136 as a function of diagnostic data 132. Prognostic data 136 may be based on a group classification of the user, such as without limitation normal LV function, only LVSD, only LVDD, and/or both LVSD and LVDD. Such prognostic data 136 may provide prognosis 124 of a user. Prognosis refers to the foretelling of a user's future from signs and symptoms. Several categories of prognoses are used in an attempt to opine about the future vocational rehabilitation of evaluees. These categories may include guarded, poor, fair, good, and excellent. Apparatus 100 simultaneously and rapidly detects LVSD and LVDD with excellent mortality prognostic information that is equivalent to that found using echocardiography. Processor 104 may output prognosis 124 based on the determination of prognostic data 136 in correlation to the categories of prognosis 124. Additionally, prognosis 124 as an output may additionally provide user with a full layout of the data as input, used, and/or generated throughout the process of diagnosis. In an embodiment, prognosis 124 may be provided via a computing device and displayed via a display screen and/or printed.

With further reference to FIG. 1, apparatus 100 includes a computing device. Computing device includes a processor 104 communicatively connected to a memory. As used in this disclosure, "communicatively connected" means connected by way of a connection, attachment or linkage between two or more relata which allows for reception and/or transmittance of information therebetween. For example, and without limitation, this connection may be wired or wireless, direct or indirect, and between two or more components, circuits, devices, systems, and the like, which allows for reception and/or transmittance of data and/or signal(s) therebetween. Data and/or signals therebetween may include, without limitation, electrical, electromagnetic, magnetic, video, audio, radio and microwave data and/or signals, combinations thereof, and the like, among others. A communicative connection may be achieved, for example and without limitation, through wired or wireless electronic, digital or analog, communication, either directly or by way of one or more intervening devices or components. Further, communicative connection may include electrically coupling or connecting at least an output of one device, component, or circuit to at least an input of another device, component, or circuit. For example, and without limitation, via a bus or other facility for intercommunication between elements of a computing device. Communicative connecting may also include indirect connections via, for example and without limitation, wireless connection, radio communication, low power wide area network, optical communication, magnetic, capacitive, or optical coupling, and the like. In some instances, the terminology "communicatively coupled" may be used in place of communicatively connected in this disclosure.

Further referring to FIG. 1, Computing device may include any computing device as described in this disclosure, including without limitation a microcontroller, microprocessor, digital signal processor (DSP) and/or system on a chip (SoC) as described in this disclosure. Computing device may include, be included in, and/or communicate with a mobile device such as a mobile telephone or smartphone. Computing device may include a single computing device operating independently, or may include two or more computing device operating in concert, in parallel, sequentially or the like; two or more computing devices may be included together in a single computing device or in two or more computing devices. Computing device may interface or communicate with one or more additional devices as described below in further detail via a network interface device. Network interface device may be utilized for connecting computing device to one or more of a variety of networks, and one or more devices. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network may employ a wired and/or a wireless mode of communication. In general, any network topology may be used. Information (e.g., data, software etc.) may be communicated to and/or from a computer and/or a computing device. Computing device may include but is not limited to, for example, a computing device or cluster of computing devices in a first location and a second computing device or cluster of computing devices in a second location. Computing device may include one or more computing devices dedicated to data storage, security, distribution of traffic for load balancing, and the like. Computing device may distribute one or more computing tasks as described below across a plurality of computing devices of computing device, which may operate in parallel, in series, redundantly, or in any other manner used for distribution of tasks or memory between computing devices. Computing device may be implemented, as a non-limiting example, using a "shared nothing" architecture.

With continued reference to FIG. 1, computing device may be designed and/or configured to perform any method, method step, or sequence of method steps in any embodiment described in this disclosure, in any order and with any degree of repetition. For instance, computing device may be configured to perform a single step or sequence repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. Computing device may perform any step or sequence of steps as described in this disclosure in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

Figure 2:
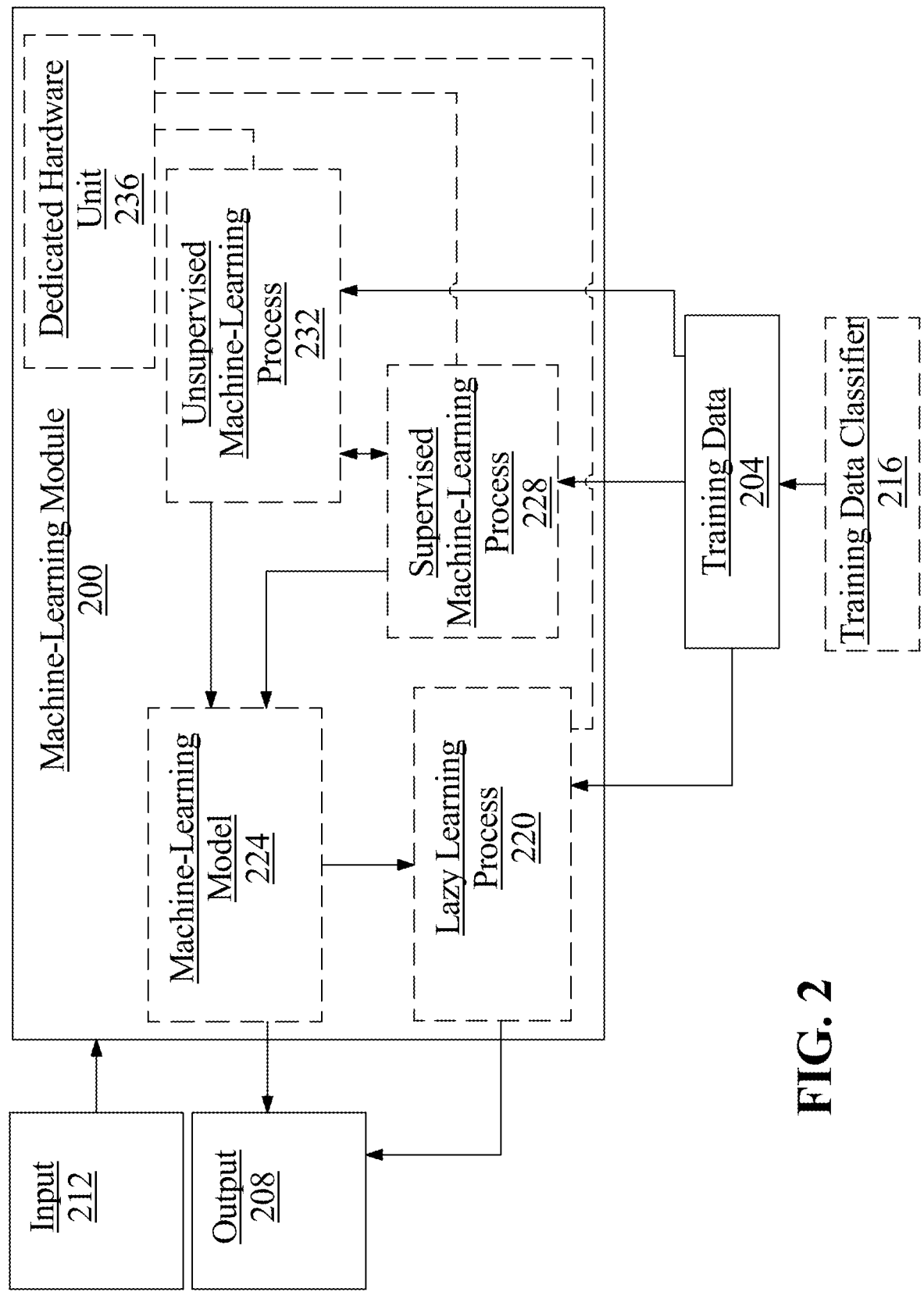
FIG. 2 is an exemplary machine-learning module.

Referring now to FIG. 2, an exemplary embodiment of a machine-learning module 200 that may perform one or more machine-learning processes as described in this disclosure is illustrated. Machine-learning module may perform determinations, classification, and/or analysis steps, methods, processes, or the like as described in this disclosure using machine learning processes. A "machine learning process," as used in this disclosure, is a process that automatedly uses training data 204 to generate an algorithm instantiated in hardware or software logic, data structures, and/or functions that will be performed by a computing device/module to produce outputs 208 given data provided as inputs 212; this is in contrast to a non-machine learning software program where the commands to be executed are determined in advance by a user and written in a programming language.

Still referring to FIG. 2, "training data," as used herein, is data containing correlations that a machine-learning process may use to model relationships between two or more categories of data elements. For instance, and without limitation, training data 204 may include a plurality of data entries, also known as "training examples," each entry representing a set of data elements that were recorded, received, and/or generated together; data elements may be correlated by shared existence in a given data entry, by proximity in a given data entry, or the like. Multiple data entries in training data 204 may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data 204 according to various correlations; correlations may indicate causative and/or predictive links between categories of data elements, which may be modeled as relationships such as mathematical relationships by machine-learning processes as described in further detail below. Training data 204 may be formatted and/or organized by categories of data elements, for instance by associating data elements with one or more descriptors corresponding to categories of data elements. As a non-limiting example, training data 204 may include data entered in standardized forms by persons or processes, such that entry of a given data element in a given field in a form may be mapped to one or more descriptors of categories. Elements in training data 204 may be linked to descriptors of categories by tags, tokens, or other data elements; for instance, and without limitation, training data 204 may be provided in fixed-length formats, formats linking positions of data to categories such as comma-separated value (CSV) formats and/or self-describing formats such as extensible markup language (XML), JavaScript Object Notation (JSON), or the like, enabling processes or devices to detect categories of data.

Alternatively or additionally, and continuing to refer to FIG. 2, training data 204 may include one or more elements that are not categorized; that is, training data 204 may not be formatted or contain descriptors for some elements of data. Machine-learning algorithms and/or other processes may sort training data 204 according to one or more categorizations using, for instance, natural language processing algorithms, tokenization, detection of correlated values in raw data and the like; categories may be generated using correlation and/or other processing algorithms. As a non-limiting example, in a corpus of text, phrases making up a number "n" of compound words, such as nouns modified by other nouns, may be identified according to a statistically significant prevalence of n-grams containing such words in a particular order; such an n-gram may be categorized as an element of language such as a "word" to be tracked similarly to single words, generating a new category as a result of statistical analysis. Similarly, in a data entry including some textual data, a person's name may be identified by reference to a list, dictionary, or other compendium of terms, permitting ad-hoc categorization by machine-learning algorithms, and/or automated association of data in the data entry with descriptors or into a given format. The ability to categorize data entries automatedly may enable the same training data 204 to be made applicable for two or more distinct machine-learning algorithms as described in further detail below. Training data 204 used by machine-learning module 200 may correlate any input data as described in this disclosure to any output data as described in this disclosure. As a non-limiting illustrative example inputs may include multi-channel sensor readings, diagnostic labels, diagnostic data, and/or the like and outputs may include prognostic data, diagnostic data, and/or the like.

Further referring to FIG. 2, training data may be filtered, sorted, and/or selected using one or more supervised and/or unsupervised machine-learning processes and/or models as described in further detail below; such models may include without limitation a training data classifier 216. Training data classifier 216 may include a "classifier," which as used in this disclosure is a machine-learning model as defined below, such as a data structure representing and/or using a mathematical model, neural net, or program generated by a machine learning algorithm known as a "classification algorithm," as described in further detail below, that sorts inputs into categories or bins of data, outputting the categories or bins of data and/or labels associated therewith. A classifier may be configured to output at least a datum that labels or otherwise identifies a set of data that are clustered together, found to be close under a distance metric as described below, or the like. A distance metric may include any norm, such as, without limitation, a Pythagorean norm. Machine-learning module 200 may generate a classifier using a classification algorithm, defined as a processes whereby a computing device and/or any module and/or component operating thereon derives a classifier from training data 204. Classification may be performed using, without limitation, linear classifiers such as without limitation logistic regression and/or naive Bayes classifiers, nearest neighbor classifiers such as k-nearest neighbors classifiers, support vector machines, least squares support vector machines, fisher's linear discriminant, quadratic classifiers, decision trees, boosted trees, random forest classifiers, learning vector quantization, and/or neural network-based classifiers. As a non-limiting example, training data classifier 216 may classify elements of training data to characterizes a sub-population, such as a cohort of persons and/or other analyzed items and/or phenomena for which a subset of training data may be selected.

Still referring to FIG. 2, processor 104 may be configured to generate a classifier using a Naïve Bayes classification algorithm. Naïve Bayes classification algorithm generates classifiers by assigning class labels to problem instances, represented as vectors of element values. Class labels are drawn from a finite set. Naïve Bayes classification algorithm may include generating a family of algorithms that assume that the value of a particular element is independent of the value of any other element, given a class variable. Naïve Bayes classification algorithm may be based on Bayes Theorem expressed as $P(A/B)=P(B/A) P(A)\div P(B)$, where $P(A/B)$ is the probability of hypothesis A given data B also known as posterior probability; $P(B/A)$ is the probability of data B given that the hypothesis A was true; $P(A)$ is the probability of hypothesis A being true regardless of data also known as prior probability of A; and $P(B)$ is the probability of the data regardless of the hypothesis. A naïve Bayes algorithm may be generated by first transforming training data into a frequency table. Processor 104 may then calculate a likelihood table by calculating probabilities of different data entries and classification labels. Processor 104 may utilize a naïve Bayes equation to calculate a posterior probability for each class. A class containing the highest posterior probability is the outcome of prediction. Naïve Bayes classification algorithm may include a gaussian model that follows a normal distribution. Naïve Bayes classification algorithm may include a multinomial model that is used for discrete counts. Naïve Bayes classification algorithm may include a Bernoulli model that may be utilized when vectors are binary.

With continued reference to FIG. 2, processor 104 may be configured to generate a classifier using a K-nearest neighbors (KNN) algorithm. A "K-nearest neighbors algorithm" as used in this disclosure, includes a classification method that utilizes feature similarity to analyze how closely out-of-sample-features resemble training data to classify input data to one or more clusters and/or categories of features as represented in training data; this may be performed by representing both training data and input data in vector forms, and using one or more measures of vector similarity to identify classifications within training data, and to determine a classification of input data. K-nearest neighbors algorithm may include specifying a K-value, or a number directing the classifier to select the k most similar entries training data to a given sample, determining the most common classifier of the entries in the database, and classifying the known sample; this may be performed recursively and/or iteratively to generate a classifier that may be used to classify input data as further samples. For instance, an initial set of samples may be performed to cover an initial heuristic and/or "first guess" at an output and/or relationship, which may be seeded, without limitation, using expert input received according to any process as described herein. As a non-limiting example, an initial heuristic may include a ranking of associations between inputs and elements of training data. Heuristic may include selecting some number of highest-ranking associations and/or training data elements.

With continued reference to FIG. 2, generating k-nearest neighbors algorithm may generate a first vector output containing a data entry cluster, generating a second vector output containing an input data, and calculate the distance between the first vector output and the second vector output using any suitable norm such as cosine similarity, Euclidean distance measurement, or the like. Each vector output may be represented, without limitation, as an n-tuple of values, where n is at least two values. Each value of n-tuple of values may represent a measurement or other quantitative value associated with a given category of data, or attribute, examples of which are provided in further detail below; a vector may be represented, without limitation, in n-dimensional space using an axis per category of value represented in n-tuple of values, such that a vector has a geometric direction characterizing the relative quantities of attributes in the n-tuple as compared to each other. Two vectors may be considered equivalent where their directions, and/or the relative quantities of values within each vector as compared to each other, are the same; thus, as a non-limiting example, a vector represented as [5, 10, 15] may be treated as equivalent, for purposes of this disclosure, as a vector represented as [1, 2, 3]. Vectors may be more similar where their directions are more similar, and more different where their directions are more divergent; however, vector similarity may alternatively or additionally be determined using averages of similarities between like attributes, or any other measure of similarity suitable for any n-tuple of values, or aggregation of numerical similarity measures for the purposes of loss functions as described in further detail below. Any vectors as described herein may be scaled, such that each vector represents each attribute along an equivalent scale of values. Each vector may be "normalized," or divided by a "length" attribute, such as a length attribute/as derived using a Pythagorean norm:

$$l = \sqrt{\sum_{i=0}^{n} a_i^2},$$

where $a_i$ is attribute number i of the vector. Scaling and/or normalization may function to make vector comparison independent of absolute quantities of attributes, while preserving any dependency on similarity of attributes; this may, for instance, be advantageous where cases represented in training data are represented by different quantities of samples, which may result in proportionally equivalent vectors with divergent values.

With further reference to FIG. 2, training examples for use as training data may be selected from a population of potential examples according to cohorts relevant to an analytical problem to be solved, a classification task, or the like. Alternatively or additionally, training data may be selected to span a set of likely circumstances or inputs for a machine-learning model and/or process to encounter when deployed. For instance, and without limitation, for each category of input data to a machine-learning process or model that may exist in a range of values in a population of phenomena such as images, user data, process data, physical data, or the like, a computing device, processor, and/or machine-learning model may select training examples representing each possible value on such a range and/or a representative sample of values on such a range. Selection of a representative sample may include selection of training examples in proportions matching a statistically determined and/or predicted distribution of such values according to relative frequency, such that, for instance, values encountered more frequently in a population of data so analyzed are represented by more training examples than values that are encountered less frequently. Alternatively or additionally, a set of training examples may be compared to a collection of representative values in a database and/or presented to a user, so that a process can detect, automatically or via user input, one or more values that are not included in the set of training examples. Computing device, processor, and/or module may automatically generate a missing training example; this may be done by receiving and/or retrieving a missing input and/or output value and correlating the missing input and/or output value with a corresponding output and/or input value collocated in a data record with the retrieved value, provided by a user and/or other device, or the like.

Continuing to refer to FIG. 2, computer, processor, and/or module may be configured to preprocess training data. "Preprocessing" training data, as used in this disclosure, is transforming training data from raw form to a format that can be used for training a machine learning model. Preprocessing may include sanitizing, feature selection, feature scaling, data augmentation and the like.

Still referring to FIG. 2, computer, processor, and/or module may be configured to sanitize training data. "Sanitizing" training data, as used in this disclosure, is a process whereby training examples are removed that interfere with convergence of a machine-learning model and/or process to a useful result. For instance, and without limitation, a training example may include an input and/or output value that is an outlier from typically encountered values, such that a machine-learning algorithm using the training example will be adapted to an unlikely amount as an input and/or output; a value that is more than a threshold number of standard deviations away from an average, mean, or expected value, for instance, may be eliminated. Alternatively or additionally, one or more training examples may be identified as having poor quality data, where "poor quality" is defined as having a signal to noise ratio below a threshold value. Sanitizing may include steps such as removing duplicative or otherwise redundant data, interpolating missing data, correcting data errors, standardizing data, identifying outliers, and the like. In a nonlimiting example, sanitization may include utilizing algorithms for identifying duplicate entries or spell-check algorithms.

As a non-limiting example, and with further reference to FIG. 2, images used to train an image classifier or other machine-learning model and/or process that takes images as inputs or generates images as outputs may be rejected if image quality is below a threshold value. For instance, and without limitation, computing device, processor, and/or module may perform blur detection, and eliminate one or more Blur detection may be performed, as a non-limiting example, by taking Fourier transform, or an approximation such as a Fast Fourier Transform (FFT) of the image and analyzing a distribution of low and high frequencies in the resulting frequency-domain depiction of the image; numbers of high-frequency values below a threshold level may indicate blurriness. As a further non-limiting example, detection of blurriness may be performed by convolving an image, a channel of an image, or the like with a Laplacian kernel; this may generate a numerical score reflecting a number of rapid changes in intensity shown in the image, such that a high score indicates clarity and a low score indicates blurriness. Blurriness detection may be performed using a gradient-based operator, which measures operators based on the gradient or first derivative of an image, based on the hypothesis that rapid changes indicate sharp edges in the image, and thus are indicative of a lower degree of blurriness. Blur detection may be performed using Wavelet-based operator, which takes advantage of the capability of coefficients of the discrete wavelet transform to describe the frequency and spatial content of images. Blur detection may be performed using statistics-based operators take advantage of several image statistics as texture descriptors in order to compute a focus level. Blur detection may be performed by using discrete cosine transform (DCT) coefficients in order to compute a focus level of an image from its frequency content.

Continuing to refer to FIG. 2, computing device, processor, and/or module may be configured to precondition one or more training examples. For instance, and without limitation, where a machine learning model and/or process has one or more inputs and/or outputs requiring, transmitting, or receiving a certain number of bits, samples, or other units of data, one or more training examples' elements to be used as or compared to inputs and/or outputs may be modified to have such a number of units of data. For instance, a computing device, processor, and/or module may convert a smaller number of units, such as in a low pixel count image, into a desired number of units, for instance by upsampling and interpolating. As a non-limiting example, a low pixel count image may have 100 pixels, however a desired number of pixels may be 128. Processor may interpolate the low pixel count image to convert the 100 pixels into 128 pixels. It should also be noted that one of ordinary skill in the art, upon reading this disclosure, would know the various methods to interpolate a smaller number of data units such as samples, pixels, bits, or the like to a desired number of such units. In some instances, a set of interpolation rules may be trained by sets of highly detailed inputs and/or outputs and corresponding inputs and/or outputs downsampled to smaller numbers of units, and a neural network or other machine learning model that is trained to predict interpolated pixel values using the training data. As a non-limiting example, a sample input and/or output, such as a sample picture, with sample-expanded data units (e.g., pixels added between the original pixels) may be input to a neural network or machine-learning model and output a pseudo replica sample-picture with dummy values assigned to pixels between the original pixels based on a set of interpolation rules. As a non-limiting example, in the context of an image classifier, a machine-learning model may have a set of interpolation rules trained by sets of highly detailed images and images that have been downsampled to smaller numbers of pixels, and a neural network or other machine learning model that is trained using those examples to predict interpolated pixel values in a facial picture context. As a result, an input with sample-expanded data units (the ones added between the original data units, with dummy values) may be run through a trained neural network and/or model, which may fill in values to replace the dummy values. Alternatively or additionally, processor, computing device, and/or module may utilize sample expander methods, a low-pass filter, or both. As used in this disclosure, a "low-pass filter" is a filter that passes signals with a frequency lower than a selected cutoff frequency and attenuates signals with frequencies higher than the cutoff frequency. The exact frequency response of the filter depends on the filter design. Computing device, processor, and/or module may use averaging, such as luma or chroma averaging in images, to fill in data units in between original data units.

In some embodiments, and with continued reference to FIG. 2, computing device, processor, and/or module may down-sample elements of a training example to a desired lower number of data elements. As a non-limiting example, a high pixel count image may have 256 pixels, however a desired number of pixels may be 128. Processor may down-sample the high pixel count image to convert the 256 pixels into 128 pixels. In some embodiments, processor may be configured to perform downsampling on data. Downsampling, also known as decimation, may include removing every Nth entry in a sequence of samples, all but every Nth entry, or the like, which is a process known as "compression," and may be performed, for instance by an N-sample compressor implemented using hardware or software. Anti-aliasing and/or anti-imaging filters, and/or low-pass filters, may be used to clean up side-effects of compression.

Further referring to FIG. 2, feature selection includes narrowing and/or filtering training data to exclude features and/or elements, or training data including such elements, that are not relevant to a purpose for which a trained machine-learning model and/or algorithm is being trained, and/or collection of features and/or elements, or training data including such elements, on the basis of relevance or utility for an intended task or purpose for a trained machine-learning model and/or algorithm is being trained. Feature selection may be implemented, without limitation, using any process described in this disclosure, including without limitation using training data classifiers, exclusion of outliers, or the like.

With continued reference to FIG. 2, feature scaling may include, without limitation, normalization of data entries, which may be accomplished by dividing numerical fields by norms thereof, for instance as performed for vector normalization. Feature scaling may include absolute maximum scaling, wherein each quantitative datum is divided by the maximum absolute value of all quantitative data of a set or subset of quantitative data. Feature scaling may include min-max scaling, in which each value X has a minimum value $X_{min}$ in a set or subset of values subtracted therefrom, with the result divided by the range of the values, give maximum value in the set or subset $$X_{max}:X_{new} = \frac{X - X_{min}}{X_{max} - X_{min}}.$$

Feature scaling may include mean normalization, which involves use of a mean value of a set and/or subset of values, $X_{mean}$ with maximum and minimum values:

$$X_{new} = \frac{X - X_{mean}}{X_{max} - X_{min}}.$$

Feature scaling may include standardization, where a difference between X and $X_{mean}$ is divided by a standard deviation σ of a set or subset of values:

$$X_{new} = \frac{X - X_{mean}}{\sigma}.$$

Scaling may be performed using a median value of a set or subset $X_{median}$ and/or interquartile range (IQR), which represents the difference between the 25$^{th}$ percentile value and the 50$^{th}$ percentile value (or closest values thereto by a rounding protocol), such as:

$$X_{new} = \frac{X - X_{median}}{IQR}.$$

Persons skilled in the art, upon reviewing the entirety of this disclosure, will be aware of various alternative or additional approaches that may be used for feature scaling.

Further referring to FIG. 2, computing device, processor, and/or module may be configured to perform one or more processes of data augmentation. "Data augmentation" as used in this disclosure is addition of data to a training set using elements and/or entries already in the dataset. Data augmentation may be accomplished, without limitation, using interpolation, generation of modified copies of existing entries and/or examples, and/or one or more generative AI processes, for instance using deep neural networks and/or generative adversarial networks; generative processes may be referred to alternatively in this context as "data synthesis" and as creating "synthetic data." Augmentation may include performing one or more transformations on data, such as geometric, color space, affine, brightness, cropping, and/or contrast transformations of images.

Still referring to FIG. 2, machine-learning module 200 may be configured to perform a lazy-learning process 220 and/or protocol, which may alternatively be referred to as a "lazy loading" or "call-when-needed" process and/or protocol, may be a process whereby machine learning is conducted upon receipt of an input to be converted to an output, by combining the input and training set to derive the algorithm to be used to produce the output on demand. For instance, an initial set of simulations may be performed to cover an initial heuristic and/or "first guess" at an output and/or relationship. As a non-limiting example, an initial heuristic may include a ranking of associations between inputs and elements of training data 204. Heuristic may include selecting some number of highest-ranking associations and/or training data 204 elements. Lazy learning may implement any suitable lazy learning algorithm, including without limitation a K-nearest neighbors algorithm, a lazy naïve Bayes algorithm, or the like; persons skilled in the art, upon reviewing the entirety of this disclosure, will be aware of various lazy-learning algorithms that may be applied to generate outputs as described in this disclosure, including without limitation lazy learning applications of machine-learning algorithms as described in further detail below.

Alternatively or additionally, and with continued reference to FIG. 2, machine-learning processes as described in this disclosure may be used to generate machine-learning models 224. A "machine-learning model," as used in this disclosure, is a data structure representing and/or instantiating a mathematical and/or algorithmic representation of a relationship between inputs and outputs, as generated using any machine-learning process including without limitation any process as described above, and stored in memory; an input is submitted to a machine-learning model 224 once created, which generates an output based on the relationship that was derived. For instance, and without limitation, a linear regression model, generated using a linear regression algorithm, may compute a linear combination of input data using coefficients derived during machine-learning processes to calculate an output datum. As a further non-limiting example, a machine-learning model 224 may be generated by creating an artificial neural network, such as a convolutional neural network comprising an input layer of nodes, one or more intermediate layers, and an output layer of nodes. Connections between nodes may be created via the process of "training" the network, in which elements from a training data 204 set are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning.

Still referring to FIG. 2, machine-learning algorithms may include at least a supervised machine-learning process 228. At least a supervised machine-learning process 228, as defined herein, include algorithms that receive a training set relating a number of inputs to a number of outputs, and seek to generate one or more data structures representing and/or instantiating one or more mathematical relations relating inputs to outputs, where each of the one or more mathematical relations is optimal according to some criterion specified to the algorithm using some scoring function. For instance, a supervised learning algorithm may include input as described above as inputs, any outputs as described above as outputs, and a scoring function representing a desired form of relationship to be detected between inputs and outputs; scoring function may, for instance, seek to maximize the probability that a given input and/or combination of elements inputs is associated with a given output to minimize the probability that a given input is not associated with a given output. Scoring function may be expressed as a risk function representing an "expected loss" of an algorithm relating inputs to outputs, where loss is computed as an error function representing a degree to which a prediction generated by the relation is incorrect when compared to a given input-output pair provided in training data 204. Persons skilled in the art, upon reviewing the entirety of this disclosure, will be aware of various possible variations of at least a supervised machine-learning process 228 that may be used to determine relation between inputs and outputs. Supervised machine-learning processes may include classification algorithms as defined above.

With further reference to FIG. 2, training a supervised machine-learning process may include, without limitation, iteratively updating coefficients, biases, weights based on an error function, expected loss, and/or risk function. For instance, an output generated by a supervised machine-learning model using an input example in a training example may be compared to an output example from the training example; an error function may be generated based on the comparison, which may include any error function suitable for use with any machine-learning algorithm described in this disclosure, including a square of a difference between one or more sets of compared values or the like. Such an error function may be used in turn to update one or more weights, biases, coefficients, or other parameters of a machine-learning model through any suitable process including without limitation gradient descent processes, least-squares processes, and/or other processes described in this disclosure. This may be done iteratively and/or recursively to gradually tune such weights, biases, coefficients, or other parameters. Updating may be performed, in neural networks, using one or more back-propagation algorithms. Iterative and/or recursive updates to weights, biases, coefficients, or other parameters as described above may be performed until currently available training data is exhausted and/or until a convergence test is passed, where a "convergence test" is a test for a condition selected as indicating that a model and/or weights, biases, coefficients, or other parameters thereof has reached a degree of accuracy. A convergence test may, for instance, compare a difference between two or more successive errors or error function values, where differences below a threshold amount may be taken to indicate convergence. Alternatively or additionally, one or more errors and/or error function values evaluated in training iterations may be compared to a threshold.

Still referring to FIG. 2, a computing device, processor, and/or module may be configured to perform method, method step, sequence of method steps and/or algorithm described in reference to this figure, in any order and with any degree of repetition. For instance, a computing device, processor, and/or module may be configured to perform a single step, sequence and/or algorithm repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. A computing device, processor, and/or module may perform any step, sequence of steps, or algorithm in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

Further referring to FIG. 2, machine learning processes may include at least an unsupervised machine-learning processes 232. An unsupervised machine-learning process, as used herein, is a process that derives inferences in datasets without regard to labels; as a result, an unsupervised machine-learning process may be free to discover any structure, relationship, and/or correlation provided in the data. Unsupervised processes 232 may not require a response variable; unsupervised processes 232 may be used to find interesting patterns and/or inferences between variables, to determine a degree of correlation between two or more variables, or the like.

Still referring to FIG. 2, machine-learning module 200 may be designed and configured to create a machine-learning model 224 using techniques for development of linear regression models. Linear regression models may include ordinary least squares regression, which aims to minimize the square of the difference between predicted outcomes and actual outcomes according to an appropriate norm for measuring such a difference (e.g. a vector-space distance norm); coefficients of the resulting linear equation may be modified to improve minimization. Linear regression models may include ridge regression methods, where the function to be minimized includes the least-squares function plus term multiplying the square of each coefficient by a scalar amount to penalize large coefficients. Linear regression models may include least absolute shrinkage and selection operator (LASSO) models, in which ridge regression is combined with multiplying the least-squares term by a factor of 1 divided by double the number of samples. Linear regression models may include a multi-task lasso model wherein the norm applied in the least-squares term of the lasso model is the Frobenius norm amounting to the square root of the sum of squares of all terms. Linear regression models may include the elastic net model, a multi-task elastic net model, a least angle regression model, a LARS lasso model, an orthogonal matching pursuit model, a Bayesian regression model, a logistic regression model, a stochastic gradient descent model, a perceptron model, a passive aggressive algorithm, a robustness regression model, a Huber regression model, or any other suitable model that may occur to persons skilled in the art upon reviewing the entirety of this disclosure. Linear regression models may be generalized in an embodiment to polynomial regression models, whereby a polynomial equation (e.g. a quadratic, cubic or higher-order equation) providing a best predicted output/actual output fit is sought; similar methods to those described above May be applied to minimize error functions, as will be apparent to persons skilled in the art upon reviewing the entirety of this disclosure.

Continuing to refer to FIG. 2, machine-learning algorithms may include, without limitation, linear discriminant analysis. Machine-learning algorithm may include quadratic discriminant analysis. Machine-learning algorithms may include kernel ridge regression. Machine-learning algorithms may include support vector machines, including without limitation support vector classification-based regression processes. Machine-learning algorithms may include stochastic gradient descent algorithms, including classification and regression algorithms based on stochastic gradient descent. Machine-learning algorithms may include nearest neighbors algorithms. Machine-learning algorithms may include various forms of latent space regularization such as variational regularization. Machine-learning algorithms may include Gaussian processes such as Gaussian Process Regression. Machine-learning algorithms may include cross-decomposition algorithms, including partial least squares and/or canonical correlation analysis. Machine-learning algorithms may include naïve Bayes methods. Machine-learning algorithms may include algorithms based on decision trees, such as decision tree classification or regression algorithms. Machine-learning algorithms may include ensemble methods such as bagging meta-estimator, forest of randomized trees, AdaBoost, gradient tree boosting, and/or voting classifier methods. Machine-learning algorithms may include neural net algorithms, including convolutional neural net processes.

Still referring to FIG. 2, a machine-learning model and/or process may be deployed or instantiated by incorporation into a program, apparatus, system and/or module. For instance, and without limitation, a machine-learning model, neural network, and/or some or all parameters thereof may be stored and/or deployed in any memory or circuitry. Parameters such as coefficients, weights, and/or biases may be stored as circuit-based constants, such as arrays of wires and/or binary inputs and/or outputs set at logic "1" and "0" voltage levels in a logic circuit to represent a number according to any suitable encoding system including twos complement or the like or may be stored in any volatile and/or non-volatile memory. Similarly, mathematical operations and input and/or output of data to or from models, neural network layers, or the like may be instantiated in hardware circuitry and/or in the form of instructions in firmware, machine-code such as binary operation code instructions, assembly language, or any higher-order programming language. Any technology for hardware and/or software instantiation of memory, instructions, data structures, and/or algorithms may be used to instantiate a machine-learning process and/or model, including without limitation any combination of production and/or configuration of non-reconfigurable hardware elements, circuits, and/or modules such as without limitation ASICs, production and/or configuration of reconfigurable hardware elements, circuits, and/or modules such as without limitation FPGAs, production and/or of non-reconfigurable and/or configuration non-rewritable memory elements, circuits, and/or modules such as without limitation non-rewritable ROM, production and/or configuration of reconfigurable and/or rewritable memory elements, circuits, and/or modules such as without limitation rewritable ROM or other memory technology described in this disclosure, and/or production and/or configuration of any computing device and/or component thereof as described in this disclosure. Such deployed and/or instantiated machine-learning model and/or algorithm may receive inputs from any other process, module, and/or component described in this disclosure, and produce outputs to any other process, module, and/or component described in this disclosure.

Continuing to refer to FIG. 2, any process of training, retraining, deployment, and/or instantiation of any machine-learning model and/or algorithm may be performed and/or repeated after an initial deployment and/or instantiation to correct, refine, and/or improve the machine-learning model and/or algorithm. Such retraining, deployment, and/or instantiation may be performed as a periodic or regular process, such as retraining, deployment, and/or instantiation at regular elapsed time periods, after some measure of volume such as a number of bytes or other measures of data processed, a number of uses or performances of processes described in this disclosure, or the like, and/or according to a software, firmware, or other update schedule. Alternatively or additionally, retraining, deployment, and/or instantiation may be event-based, and may be triggered, without limitation, by user inputs indicating sub-optimal or otherwise problematic performance and/or by automated field testing and/or auditing processes, which may compare outputs of machine-learning models and/or algorithms, and/or errors and/or error functions thereof, to any thresholds, convergence tests, or the like, and/or may compare outputs of processes described herein to similar thresholds, convergence tests or the like. Event-based retraining, deployment, and/or instantiation may alternatively or additionally be triggered by receipt and/or generation of one or more new training examples; a number of new training examples may be compared to a preconfigured threshold, where exceeding the preconfigured threshold may trigger retraining, deployment, and/or instantiation.

Still referring to FIG. 2, retraining and/or additional training may be performed using any process for training described above, using any currently or previously deployed version of a machine-learning model and/or algorithm as a starting point. Training data for retraining may be collected, preconditioned, sorted, classified, sanitized or otherwise processed according to any process described in this disclosure. Training data may include, without limitation, training examples including inputs and correlated outputs used, received, and/or generated from any version of any system, module, machine-learning model or algorithm, apparatus, and/or method described in this disclosure; such examples may be modified and/or labeled according to user feedback or other processes to indicate desired results, and/or may have actual or measured results from a process being modeled and/or predicted by system, module, machine-learning model or algorithm, apparatus, and/or method as "desired" results to be compared to outputs for training processes as described above.

Redeployment may be performed using any reconfiguring and/or rewriting of reconfigurable and/or rewritable circuit and/or memory elements; alternatively, redeployment may be performed by production of new hardware and/or software components, circuits, instructions, or the like, which may be added to and/or may replace existing hardware and/or software components, circuits, instructions, or the like.

Further referring to FIG. 2, one or more processes or algorithms described above may be performed by at least a dedicated hardware unit 232. A "dedicated hardware unit," for the purposes of this figure, is a hardware component, circuit, or the like, aside from a principal control circuit and/or processor performing method steps as described in this disclosure, that is specifically designated or selected to perform one or more specific tasks and/or processes described in reference to this figure, such as without limitation preconditioning and/or sanitization of training data and/or training a machine-learning algorithm and/or model. A dedicated hardware unit 232 may include, without limitation, a hardware unit that can perform iterative or massed calculations, such as matrix-based calculations to update or tune parameters, weights, coefficients, and/or biases of machine-learning models and/or neural networks, efficiently using pipelining, parallel processing, or the like; such a hardware unit may be optimized for such processes by, for instance, including dedicated circuitry for matrix and/or signal processing operations that includes, e.g., multiple arithmetic and/or logical circuit units such as multipliers and/or adders that can act simultaneously and/or in parallel or the like. Such dedicated hardware units 232 may include, without limitation, graphical processing units (GPUs), dedicated signal processing modules, FPGA or other reconfigurable hardware that has been configured to instantiate parallel processing units for one or more specific tasks, or the like, A computing device, processor, apparatus, or module may be configured to instruct one or more dedicated hardware units 232 to perform one or more operations described herein, such as evaluation of model and/or algorithm outputs, one-time or iterative updates to parameters, coefficients, weights, and/or biases, and/or any other operations such as vector and/or matrix operations as described in this disclosure.

Figure 3:
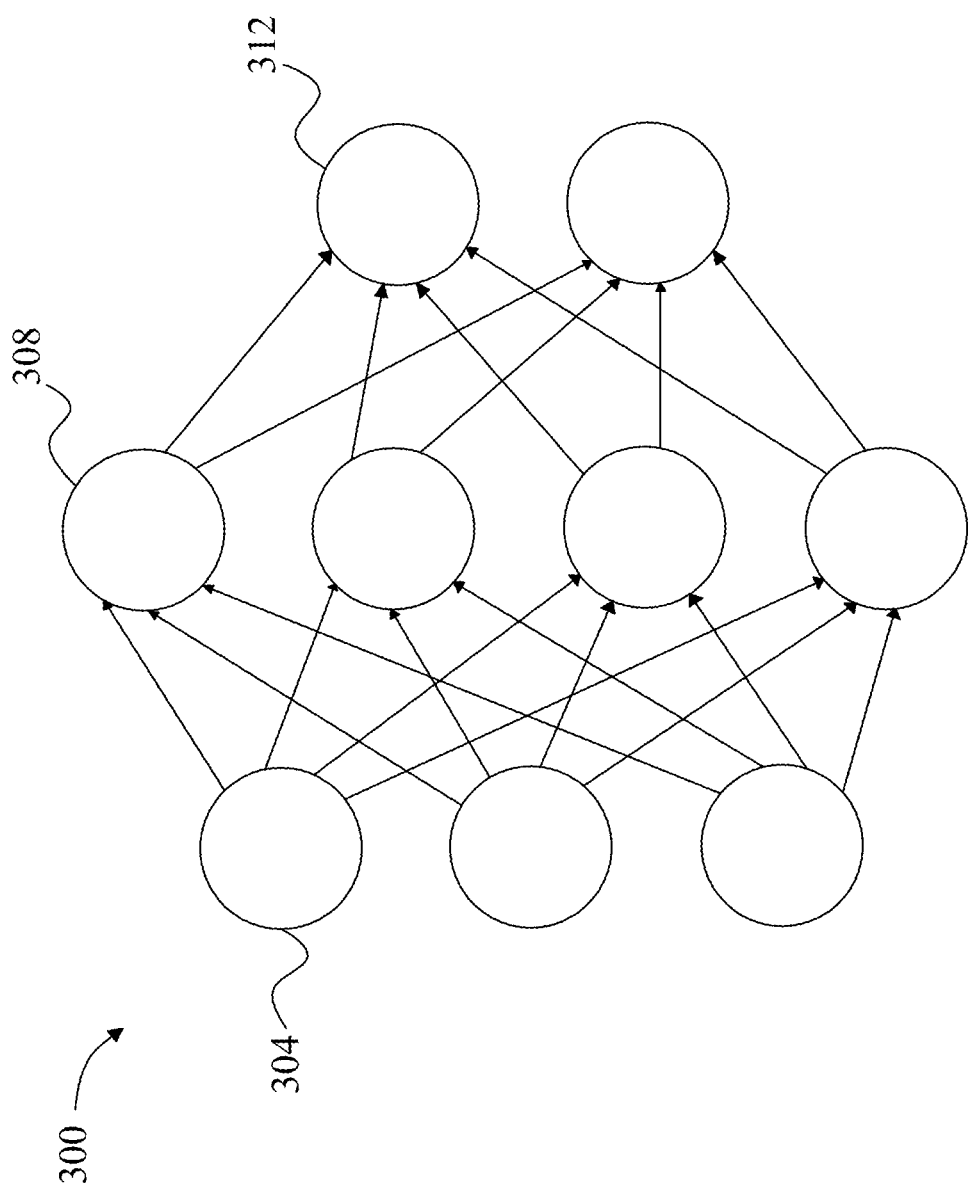
FIG. 3 is an exemplary neural network.

Referring now to FIG. 3, an exemplary embodiment of neural network 300 is illustrated. A neural network 300 also known as an artificial neural network, is a network of "nodes," or data structures having one or more inputs, one or more outputs, and a function determining outputs based on inputs. Such nodes may be organized in a network, such as without limitation a convolutional neural network, including an input layer of nodes 304, one or more intermediate layers 308, and an output layer of nodes 312. Connections between nodes may be created via the process of "training" the network, in which elements from a training dataset are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning. Connections may run solely from input nodes toward output nodes in a "feed-forward" network or may feed outputs of one layer back to inputs of the same or a different layer in a "recurrent network." As a further non-limiting example, a neural network may include a convolutional neural network comprising an input layer of nodes, one or more intermediate layers, and an output layer of nodes. A "convolutional neural network," as used in this disclosure, is a neural network in which at least one hidden layer is a convolutional layer that convolves inputs to that layer with a subset of inputs known as a "kernel," along with one or more additional layers such as pooling layers, fully connected layers, and the like.

Figure 4:
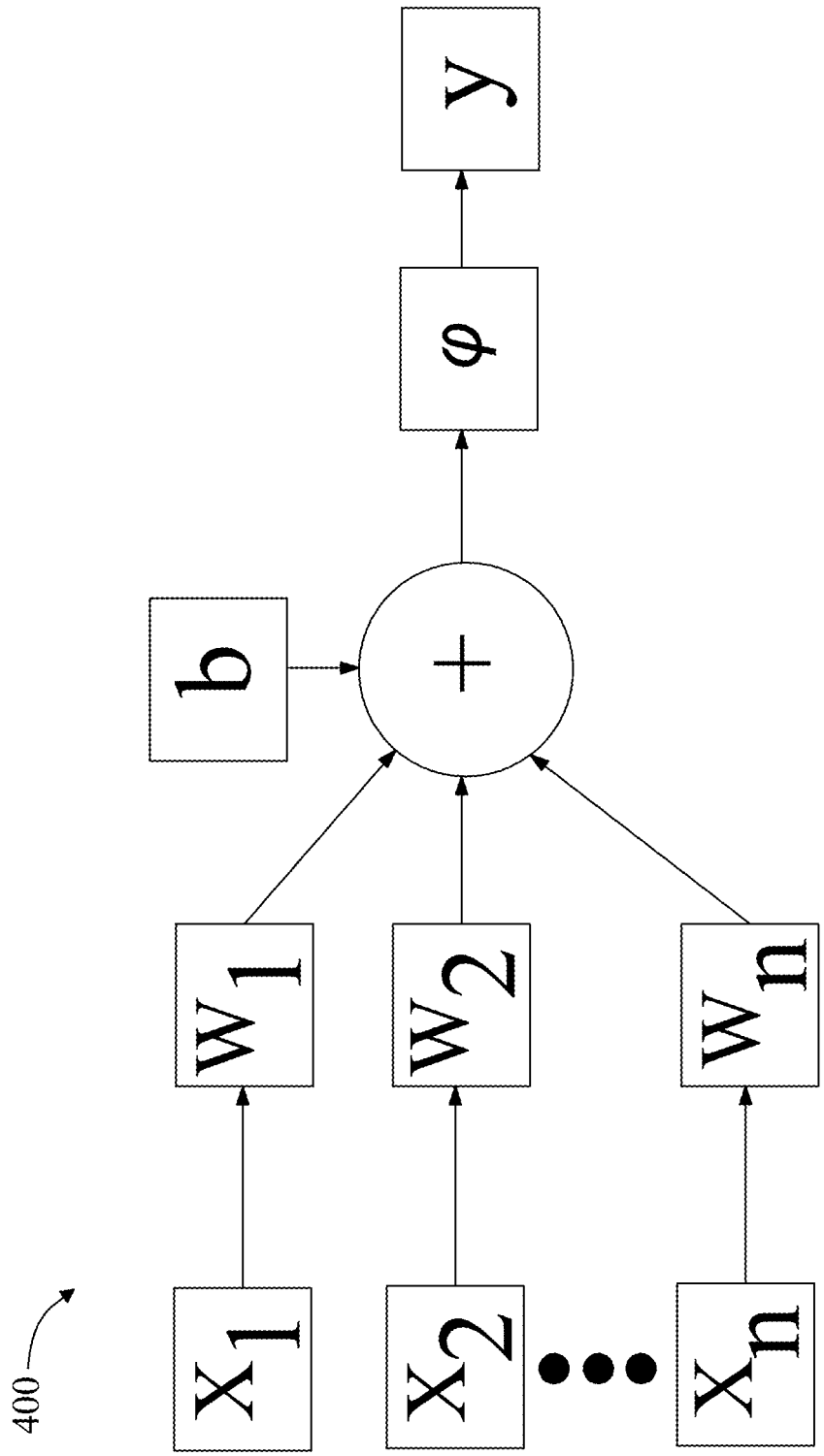
FIG. 4 is an exemplary node of a neural network.

Referring now to FIG. 4, an exemplary embodiment of a node 4400 of a neural network is illustrated. A node may include, without limitation a plurality of inputs $x_i$ that May receive numerical values from inputs to a neural network containing the node and/or from other nodes. Node may perform one or more activation functions to produce its output given one or more inputs, such as without limitation computing a binary step function comparing an input to a threshold value and outputting either a logic 1 or logic 0 output or something equivalent, a linear activation function whereby an output is directly proportional to the input, and/or a non-linear activation function, wherein the output is not proportional to the input. Non-linear activation functions may include, without limitation, a sigmoid function of the form $$f(x) = \frac{1}{1 - e^{-x}}$$

given input x, a tanh (hyperbolic tangent) function, of the form $$\frac{e^x - e^{-x}}{e^x + e^{-x}},$$

a tanh derivative function such as $f(x)=\tanh^2(x)$, a rectified linear unit function such as $f(x)=\max(0, x)$, a "leaky" and/or "parametric" rectified linear unit function such as $f(x)=\max(ax, x)$ for some a, an $$f(x) = \begin{cases} x & \text{for } x \geq 0 \\ \alpha(e^x - 1) & \text{for } x < 0 \end{cases}$$

exponential linear units function such as for some value of $\alpha$ (this function may be replaced and/or weighted by its own derivative in some embodiments), a softmax function such as $$f(x_i) = \frac{e^x}{\sum_i x_i}$$

where the inputs to an instant layer are $x_i$, a swish function such as $f(x)=x*\text{sigmoid}(x)$, a Gaussian error linear unit function such as $f(x)=a(1+\tanh(\sqrt{2/\pi}(x+bx^r)))$ for some values of a, b, and r, and/or a scaled exponential linear unit function such as $$f(x) = \lambda \begin{cases} \alpha(e^x - 1) & \text{for } x < 0 \\ x & \text{for } x \geq 0 \end{cases}.$$

Fundamentally, there is no limit to the nature of functions of inputs $x_i$ that may be used as activation functions. As a non-limiting and illustrative example, node may perform a weighted sum of inputs using weights $w_i$ that are multiplied by respective inputs $x_i$. Additionally or alternatively, a bias b may be added to the weighted sum of the inputs such that an offset is added to each unit in the neural network layer that is independent of the input to the layer. The weighted sum may then be input into a function φ, which may generate one or more outputs y. Weight $w_i$ applied to an input $x_i$ may indicate whether the input is "excitatory," indicating that it has strong influence on the one or more outputs y, for instance by the corresponding weight having a large numerical value, and/or a "inhibitory," indicating it has a weak effect influence on the one more inputs y, for instance by the corresponding weight having a small numerical value. The values of weights $w_i$ may be determined by training a neural network using training data, which may be performed using any suitable process as described above.

Particular Implementation for LVDD

Study Introduction

Now referring to FIGS. 5A-5E, illustrated are figures pertaining to methods and results of an example study performed to assess the performance of an implemented artificial intelligence-enabled ECG prediction model for left ventricular diastolic function and filling pressure. In this study of a particular implementation of an AI-supported diagnostic assessment, the diagnostic assessment was based on 12-lead ECG to predict diastolic function and increased filling pressure determined by echocardiography, and then to evaluate its associations with all-cause mortality.

In some cases, left ventricular diastolic function becomes abnormal in myocardial diseases. With the worsening of diastolic function, filling pressure may rise even while ejection fraction is preserved. Documentation of increased left ventricular filling pressure may be used in diagnosis of heart failure with preserved ejection fraction. Moreover, elevated diastolic filling pressure may be associated with heart failure symptoms and higher mortality in patients with myocardial infarction, valvular diseases, and/or cardiomyopathies. Diastolic function may be evaluated by echocardiography. However, such assessment of diastolic function may require a skilled sonographer and/or cardiologist with advanced training in echocardiographic interpretation. Results of a diastolic function assessment may be equivocal in a substantial proportion of patients. Twelve-lead electrocardiogramay be more widely performed with little cost.

Study Method

Data Study Population

The following method was followed regarding an exemplary study of a particular implementation of an AI-supported diagnostic assessment tool. Within the study adults were identified (age ≥18 years) who had at least one ECG and transthoracic echocardiogram with echocardiographic assessment of diastolic function performed within 14 days of ECG between September 2001 and April 2023 from the Mayo Clinic Unified Data Platform. No exclusion criteria were applied. All ECGs were measured with 250 or 500 Hz sampling rate using a GE-Marquette machine for a standard 10-s 12-lead ECG and were stored in the GE-MUSE system (Marquette, WI, USA). ECGs with an original sampling rate of 250 Hz were up-sampled to 500 Hz prior to analysis. The final cohort (n=219,462) was divided into training (n=98,736, 45%), validation (n=21,963, 10%), and testing (n=98,763, 45%) sets. The final model was tested in 55,248 patients with indeterminate diastolic function by echocardiography.

Filling Pressure and Diastolic Function Grading Assessment

The following method was followed regarding the exemplary study of the particular implementation of an AI-supported diagnostic assessment tool. As recommended by the 2016 ASE/EACVI diastolic function guidelines, four parameters were used to evaluate diastolic function: e', E/e', tricuspid regurgitation velocity, and left atrial volume index, with a minor modification (See FIG. 5P). When 3 or all of the above four parameters were abnormal, filling pressure was determined to be elevated. This group was subsequently separated into grade 2 or 3 based on E/A of 2.0. When 3 or all parameters were normal, filling pressure was determined to be normal. These patients were further separated into normal diastolic function or grade 1 according to the E/A ratio separating the value of 0.8. When the four parameters were split into 2 normal and 2 abnormal, diastolic function was assessed as indeterminate. Diastolic function and filling pressure were labeled based on the above algorithms for all subjects.

Overview of AI Model

The following method was followed regarding overview of AI model in the exemplary study of the particular implementation of an AI-supported diagnostic assessment tool. The primary goal of developing the AI-enabled ECG was to predict left ventricular filling pressure and diastolic function grade using a 12-lead ECG. As model architecture, convolutional neural networks of the ResNet-1831 were implemented. Each ECG has 12×5000 matrix that consists of 12-lead ECG by 10-s sampled at 500 Hz. For input of the network, the ECG were split by 2 s and average the output values from 5 splits. The network was trained with a learning rate of 0.001 and Adam optimizer for 20 epochs. The validation performance was converged before the $20^{th}$ epoch. The final model was chosen according to the AUC value from the validation set for increased filling pressure. The model was trained as a multi-class model with four outputs representing the four grades of diastolic function and the sum of four outputs was 1. Normal and grade 1 were considered normal filling pressure, and grades 2 and 3 were considered increased filling pressure. While the model outputs four values, the sum of the outputs of normal and grade 1 represents the output of normal filling pressure, and the sum of grades 2 and 3 outputs represents the output of increased filling pressure. Likewise, the sum of the outputs of normal and increased filling pressures was 1. Using the sum of each two classes, the multi-class model was converted to a binary model and an existing index was applied to the final output value. Likewise, an aggregated output and a label for grade 1 or above, grade 2 or above, and grade 3, respectively, were created to evaluate the performance with the ordinal scale of diastolic function grade. Additionally, deep neural networks were trained with the same architecture for single-lead ECG and single-lead median beat. Since Lead I is most widely measured for wearable devices, Lead I is used for both models. Single-lead median beat is the representative beat for 10-s and the duration is 1.2 s. Reported, was the hold-out test set result from the selected model.

Statistical Analysis

The following method was followed regarding statistical analysis in the exemplary study of the particular implementation. The model's ability was assessed by calculating the AUC of the ROC curve, sensitivity, specificity, PPV, NPV, and accuracy. Two-sided 95% confidence intervals were calculated. It was assessed whether the model discriminates the risk of all-cause mortality using the Kaplan-Meier estimate and compared it with the log-rank test. Multivariable Cox proportional-hazards models were developed. Age, sex, and comorbidities (diabetes, hypertension, obesity, myocardial infarction, congestive heart failure, cerebrovascular disease, chronic pulmonary disease, and renal disease) were used for the adjustment of the hazard ratio. For continuous variables, groups were compared using Student's t-test. For categorical variables, chi-squared tests were used. A two-tailed P-value <0.001 was considered significant, however, its interpretation was carefully and comprehensively made because of the large sample size.

Study Results

With further reference to the particular implementation, 274,710 patients having an ECG and echocardiographic diastolic function assessment within 14 days were identified with no exclusion criteria. Echocardiography determination of diastolic function was possible in 219,462 patients (80%) but was indeterminate in 55,248 patients (20%). Baseline patient characteristics were similar among training, validation, and testing groups (Table 3). There were 20,264 patients with left ventricular ejection fraction <0.001, Table 1). Similarly, patients identified as having increased filling pressure by AI-ECG, had more comorbidities (p<0.001, Table 4).

TABLE 1

Table 1. Patient characteristics of four diastolic grade groups determined by echocardiography in test set.

| | Test (n = 98,763) | | | |
|---|---|---|---|---|
| | Normal (n = 57,301) | Grade 1 (n = 19,579) | Grade 2 (n = 17,815) | Grade 3 (n = 4068) |
| Age, year | 54.0 ± 16.0 | 69.0 ± 10.8 | 73.9 ± 12.4 | 69.2 ± 14.6 |
| Female sex, number (%) | 28,873 (50.4%) | 9678 (49.4%) | 10,049 (56.4%) | 1493 (36.7%) |
| Myocardial infarction, number (%) | 3269 (5.7%) | 1735 (8.9%) | 2746 (15.5%) | 705 (17.4%) |
| Congestive heart failure, number (%) | 4774 (8.4%) | 2598 (13.3%) | 6777 (38.1%) | 2633 (64.9%) |
| Cerebrovascular disease, number (%) | 3835 (6.7%) | 2340 (12.0%) | 2537 (14.3%) | 465 (11.5%) |
| Chronic pulmonary disease, number (%) | 6444 (11.3%) | 3097 (15.9%) | 4370 (24.6%) | 1051 (25.9%) |
| Diabetes, number (%) | 5778 (10.1%) | 3356 (17.1%) | 5086 (28.5%) | 1206 (29.6%) |
| Renal disease, number (%) | 4786 (8.4%) | 2633 (13.5%) | 5288 (29.8%) | 1406 (34.7%) |
| Hypertension, number (%) | 19,673 (34.4%) | 10,779 (55.2%) | 11,990 (67.5%) | 2378 (58.6%) |
| Obesity, number (%) | 18,141 (31.7%) | 6630 (33.9%) | 6385 (35.8%) | 1423 (35.0%) |

Values are n (%) or mean ± SD. Obesity was defined as body mass index ≥30. Renal disease includes any stages of chronic kidney disease, hypertensive kidney disease, glomerulonephritis, nephritic syndrome, hereditary nephropathy, end-stage renal disease, unspecified kidney failure, dialysis, and kidney transplant status.

TABLE 2

Table 2.
Model performance for filling pressure and diastolic function
from the AI-enabled ECG in test set with AUC, sensitivity, specificity, PPV, and NPV.

| Class | Prevalence | AUC | Sensitivity (%) | Specificity (%) | PPV (%) | NPV (%) |
|---|---|---|---|---|---|---|
| Increased filling pressure | 22.2% (21,883/98,763) | 0.911 | 83.2 | 82.9 | 58.1 | 94.5 |
| Grade 1 or above | 42% (41,462/98,763) | 0.847 | 76.6 | 75.3 | 69.2 | 81.6 |
| Grade 2 or above | 22.2% (21,883/98,763) | 0.911 | 83.2 | 82.9 | 58.1 | 94.5 |
| Grade 3 | 4.1% (4068/98,763) | 0.943 | 89.8 | 86.0 | 21.6 | 99.5 |

Thresholds for grade 1 or above, grade 2 or above (increased filling pressure), and grade 3 are 0.443, 0.264, and 0.058, respectively, to evaluate the performance.

TABLE 3

| | Overall (n = 219,462) | | |
|---|---|---|---|
| | Training (n = 98,736) | Validation (n = 21,963) | Test (n = 98,763) |
| Age, y | 61.0 ± 16.8 | 60.8 ± 16.8 | 61.2 ± 16.8 |
| Female sex, Number (%) | 50,574 (51.2%) | 11,164 (50.8%) | 50,093 (50.7%) |
| Myocardial infarction, Number (%) | 8,513 (8.6%) | 1,914 (8.7%) | 8,455 (8.6%) |
| Congestive heart failure, Number (%) | 16,797 (17.1%) | 3,833 (17.5%) | 16,782 (17.0%) |
| Cerebrovascular disease, Number (%) | 9,082 (9.2%) | 1,970 (9.0%) | 9,177 (9.3%) |
| Chronic pulmonary disease, Number (%) | 14,869 (15.1%) | 3,277 (15.0%) | 14,962 (15.2%) |
| Diabetes Mellitus, Number (%) | 15,598 (15.8%) | 3,504 (16.0%) | 15,426 (15.6%) |
| Renal disease, Number (%) | 13,825 (14.0%) | 3,086 (14.1%) | 14,113 (14.3%) |
| Hypertension, Number (%) | 44,639 (45.3%) | 9,888 (45.1%) | 44,820 (45.5%) |
| Obesity, Number (%) | 32,696 (33.1%) | 7,280 (33.1%) | 32,579 (33.0%) |

TABLE 4

| | Test (n = 98,763) | | | |
|---|---|---|---|---|
| AI-ECG diastolic function grade | Normal (n = 64,439) | Grade 1 (n = 10,791) | Grade 2 (n = 19,282) | Grade 3 (n = 4,251) |
| Age, year | 55.6 ± 16.1 | 70.0 ± 10.5 | 73.0 ± 12.7 | 69.8 ± 4.7 |
| Female sex, Number (%) | 32,801 (50.9%) | 5,338 (49.5%) | 10,340 (53.6%) | 1,614 (38.0%) |
| Myocardial infarction, Number (%) | 3,674 (5.7%) | 1,071 (9.9%) | 2,897 (15.1%) | 813 (19.2%) |
| Congestive heart failure, Number (%) | 5,425 (8.4%) | 1,414 (13.1%) | 7,012 (36.5%) | 2,931 (69.1%) |
| Cerebrovascular disease, Number (%) | 4,513 (7.0%) | 1,341 (12.4%) | 2,793 (14.5%) | 530 (12.5%) |
| Chronic pulmonary disease, Number (%) | 7,848 (12.2%) | 1,760 (16.3%) | 4,164 (21.7%) | 1,190 (28.1%) |
| Diabetes, Number (%) | 6,961 (10.8%) | 1,901 (17.6%) | 5,188 (26.9%) | 1,376 (32.4%) |
| Renal disease, Number (%) | 5,694 (8.9%) | 1,427 (13.2%) | 5,329 (27.7%) | 1,663 (39.2%) |
| Hypertension, Number (%) | 23,310 (36.3%) | 6,151 (57.1%) | 12,825 (66.7%) | 2,534 (59.7%) |
| Obesity, Number (%) | 20,356 (31.6%) | 4,060 (37.6%) | 6,847 (35.5%) | 1,316 (31.0%) |

AI-Enabled ECG Classification Performance

Figure 5A:
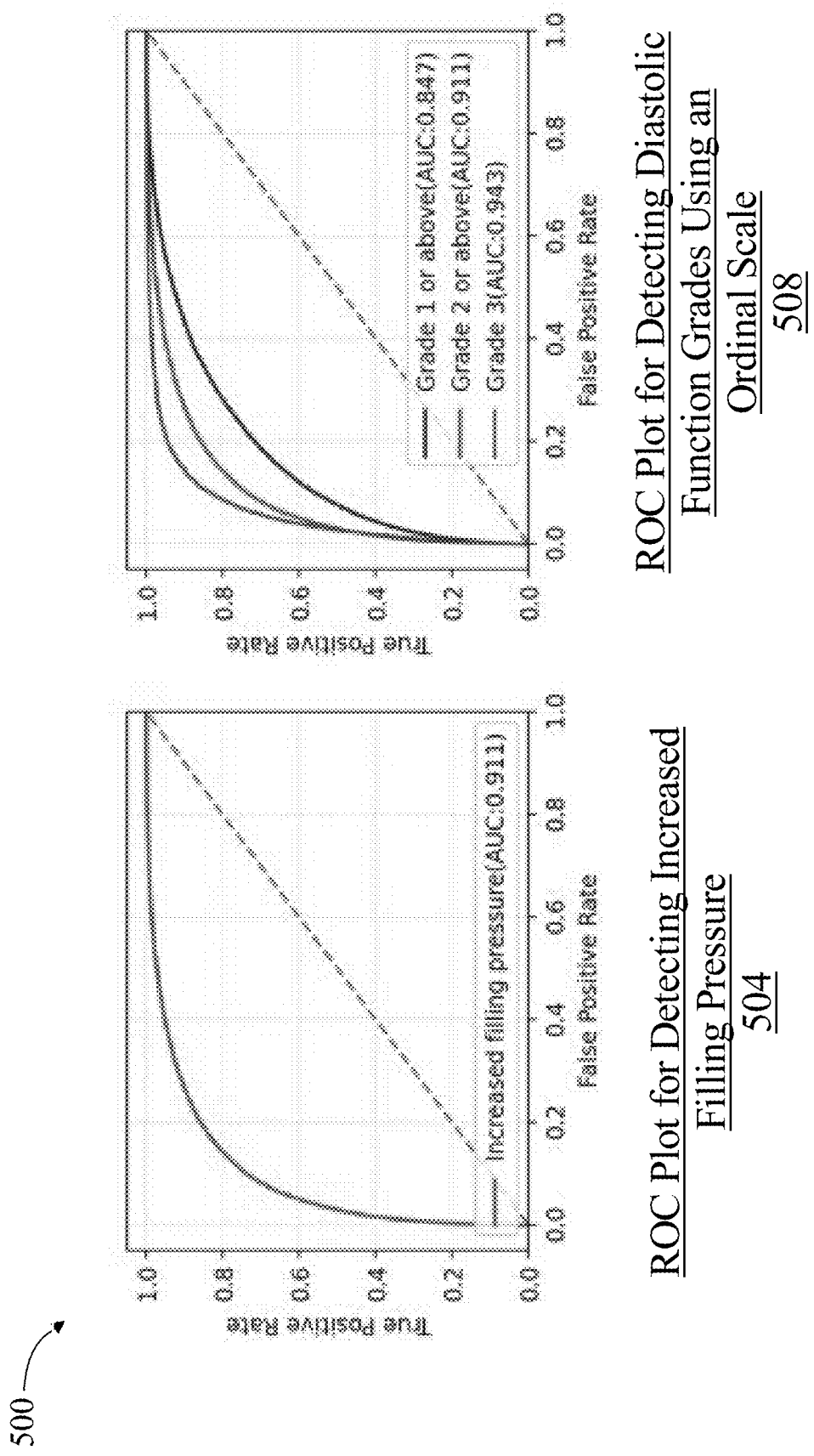
FIGS. 5A-5P pertain to methods and results of an example study performed to assess the performance of an implemented artificial intelligence-enabled ECG for left ventricular diastolic function and filling pressure.
Figure 5B:
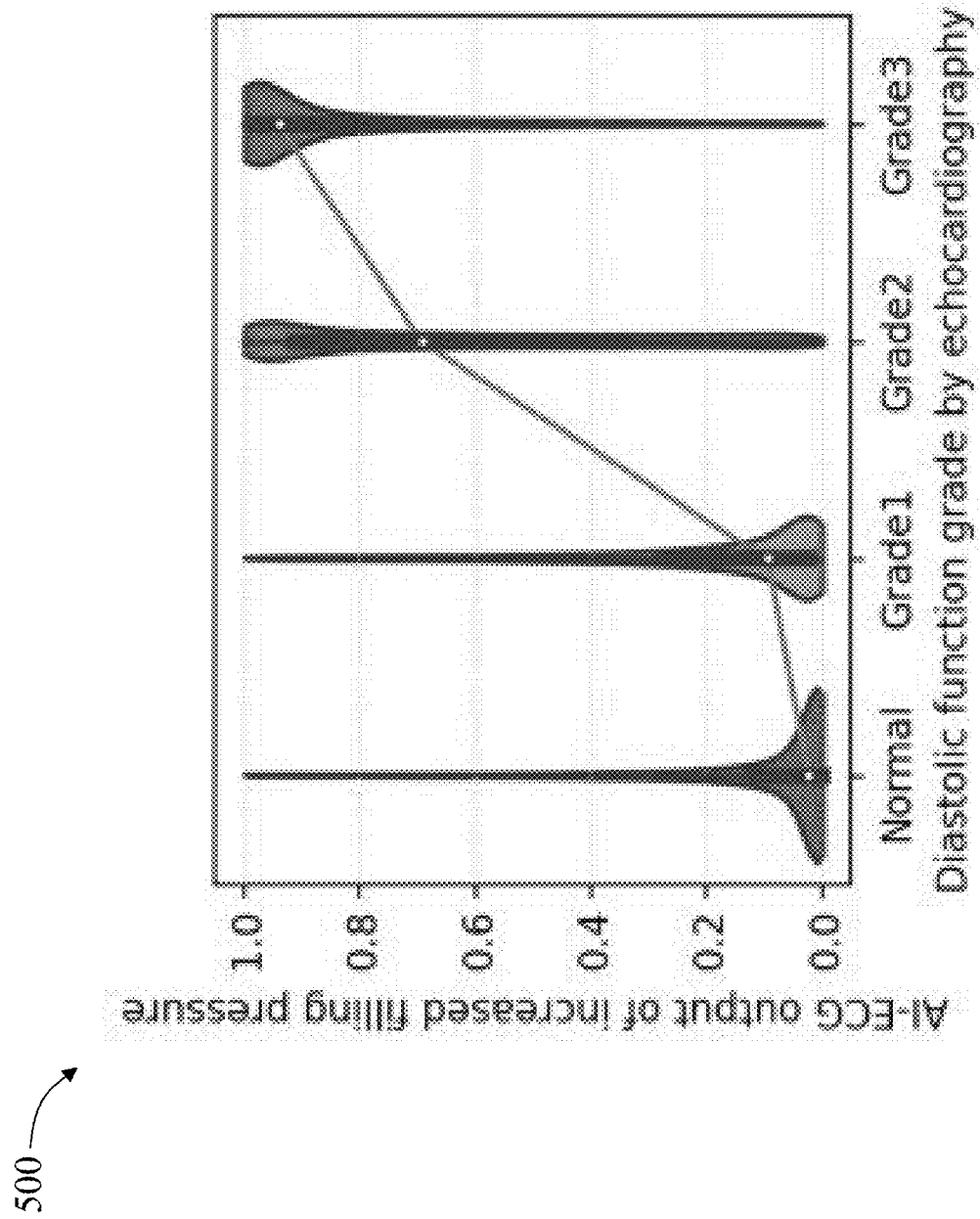

In continued reference to the particular implementation, the test set, the AI-enabled ECG for predicting echocardiography, determined increased filling pressure had an area under the curve (AUC) of the receiver operating characteristic (ROC) curve of 0.911 (95% CI: 0.909-0.914) with a sensitivity of 83.2%, specificity of 82.9%, positive predictive value (PPV) of 58%, and negative predictive value (NPV) of 94.5% with the threshold of 0.26, and prevalence of 22.2% (FIG. 1a and Table 2). The AI-enabled ECG's AUCs for grade ≥1, grade ≥2, and grade 3 were 0.847 (95% CI: 0.844-0.85), 0.911 (95% CI: 0.909-0.914), and 0.943 (95% CI: 0.938-0.948) at thresholds of 0.443, 0.264, 0.058, respectively (See FIG. 5 ROC Plot 508 and Table 2). The median output values for the increased filling pressure from the model were significantly higher in the diastolic function grades 2 and 3 by echocardiography compared to normal and grade 1 (FIG. 5B). The model showed higher specificity in younger patients and among patients with more comorbidities there was a tendency towards decreased specificity (See FIG. 5F-5F3 and Table 3). Echocardiographic diastolic parameters significantly differed between patients identified by the model to have increased and normal filling pressure patients in the testing (See FIG. 5H). Those diastolic parameters were almost identical in patients with normal filling pressure determined by AI-ECG and echocardiography.

Those values in patients with increased filling pressure by both AI-ECG and echocardiography were consistent with grade 2-3 diastolic dysfunction and significantly different from values in patients with normal filling pressure. In the indeterminate group, all echocardiographic diastolic parameters except e' velocity were significantly different between normal and increased filling pressure determined by AI-ECG (See FIG. 5I). The AI-enabled ECG trained exclusively by ECG Lead I had AUCs of 0.804 (95% CI: 0.801-0.807), 0.875 (95% CI: 0.872-0.878), and 0.915 (95% CI: 0.909-0.921) for grade ≥1, grade ≥2, and grade 3, respectively. The AI-enabled ECG trained by ECG Lead I median beat had AUCs of 0.763 (95% CI: 0.76-0.766), 0.834 (95% CI: 0.83-0.837), and 0.877 (95% CI: 0.87-0.884), respectively. The AUCs of AI-enabled ECG between before and after the median year of the echocardiography exam, i.e., 2014, were 0.856 and 0.839 for grade ≥1, 0.91 and 0.913 for grade ≥2, and 0.944 and 0.942 for grade 3, respectively. (See FIG. 5J).

AI-ECG (+) and echocardiography (−), and false negative (FN; AI-ECG (−) and echocardiography (+)). While TP had the worst mortality and TN the best in all 3 diastolic dysfunction groups, FP and FN groups had a similar mortality in grade ≥1 or ≥2, but FP was found to have the same mortality as that of TP which was significantly worse than that of FN (HR 1.402, 95% CI 1.281-1.535) for grade 3 after adjusting for age, sex, and comorbidities. The risk of death was also greater among patients in the indeterminate group with higher filling pressure predicted from the AI-enabled ECG (HR 1.34, 95% CI 1.298-1.383). Among patients with normal filling pressure by the AI-enabled ECG, grade 1 dysfunction had worse survival than normal grade in both the testing and the indeterminate groups. Among patients with grade 1 diastolic dysfunction by echocardiography, 54.7% were classified as normal by the AI-enabled ECG. Those who were labeled as normal had lower risk of death than patients who labeled as grade 1 dysfunction by the

TABLE 5

| Comorbidity | Class | Prevalence | AUCROC | Sensitivity | Specificity | PPV | NPV |
| --- | --- | --- | --- | --- | --- | --- | --- |
| Hypertension | Grade 1 | Y | 0.81 | 0.8 | 0.65 | 0.72 | 0.74 |
| | or above | N | 0.86 | 0.67 | 0.86 | 0.6 | 0.89 |
| | Grade 2 | Y | 0.88 | 0.84 | 0.76 | 0.6 | 0.92 |
| | or above | N | 0.94 | 0.8 | 0.91 | 0.5 | 0.98 |
| | Grade 3 | Y | 0.93 | 0.9 | 0.81 | 0.21 | 0.99 |
| | | N | 0.97 | 0.9 | 0.93 | 0.25 | 1 |
| Obesity | Grade 1 | Y | 0.82 | 0.77 | 0.7 | 0.67 | 0.79 |
| | or above | N | 0.86 | 0.76 | 0.78 | 0.7 | 0.83 |
| | Grade 2 | Y | 0.9 | 0.82 | 0.81 | 0.58 | 0.93 |
| | or above | N | 0.92 | 0.84 | 0.84 | 0.58 | 0.95 |
| | Grade 3 | Y | 0.94 | 0.9 | 0.85 | 0.22 | 0.99 |
| | | N | 0.94 | 0.9 | 0.86 | 0.21 | 1 |
| Diabetes | Grade 1 | Y | 0.81 | 0.83 | 0.61 | 0.75 | 0.71 |
| | or above | N | 0.85 | 0.74 | 0.78 | 0.66 | 0.84 |
| | Grade 2 | Y | 0.89 | 0.86 | 0.73 | 0.65 | 0.9 |
| | or above | N | 0.91 | 0.81 | 0.85 | 0.54 | 0.95 |
| | Grade 3 | Y | 0.91 | 0.92 | 0.76 | 0.22 | 0.99 |
| | | N | 0.95 | 0.88 | 0.89 | 0.21 | 1 |

Survival Analysis

Further referencing the particular implementation, death from any cause was observed in 20,223 (20.5%) of 98,763 patients in the test group and 18,224 (33.0%) of 55,248 in the indeterminate group over a median follow-up of 5.9 years (IQR 2.7, 10.2) and 5.7 years (IQR 2.6, 9.9), respectively. Mortality was significantly higher in patients with increased filling pressure compared to those with normal filling pressure predicted by the AI-enabled ECG after adjusting for age, sex, and comorbidities (hazard ratio (HR) 1.7, 95% CI 1.645-1.757; FIG. 3a). This was similar to the mortality predicted by echocardiographically determined filling pressure (HR 1.65, 95% CI: 1.597-1.705; See FIG. 5C echocardiography (test) 516). All-cause mortality was also predicted by diastolic function grading determined by ECG with significantly higher mortality in patients with grade 2 and 3 diastolic dysfunction compared to those with normal or grade 1 diastolic dysfunction (HR 1.299, 95% CI 1.279-1.319, See FIG. 5D, AI-enabled (test) 512). Diastolic function grading based directly upon echocardiographic parameters had a similar prognostic value (HR 1.298, 95% CI 1.277-1.32) even after adjusting for age, sex, and comorbidities. Since some patients had a discordance between AI-ECG and echocardiography determination of diastolic function, the study patients were separated into four groups in each category of diastolic dysfunction: true positive (TP; AI-ECG (+) and echocardiography (+), true negative (TN; AI-ECG (−) and echocardiography (−), false positive (FP; AI-enabled ECG. The AI-enabled ECG successfully discriminated risk of death among specific age groups (≤50 years, 50<age <70 years, age ≥70 years) even after adjusting for age, sex, and comorbidities. Study Figures Now referring to FIG. 5A, shown are AI-enabled ECG ROC curves for diastolic function grade and filling pressure. ROC plot for detecting increased filling pressure 504 and ROC plot for detecting diastolic function grades using an ordinal scale 508 are specifically illustrated.

Now referring to FIG. 5B, shown is an AI-enabled ECG output distribution for increased filling pressure by estimated diastolic function grade. The distribution was described as a box plot with a kernel density plot. Box plots may show median and first and third quartiles with outliers as 1.5 times IQR.

Figure 5C:
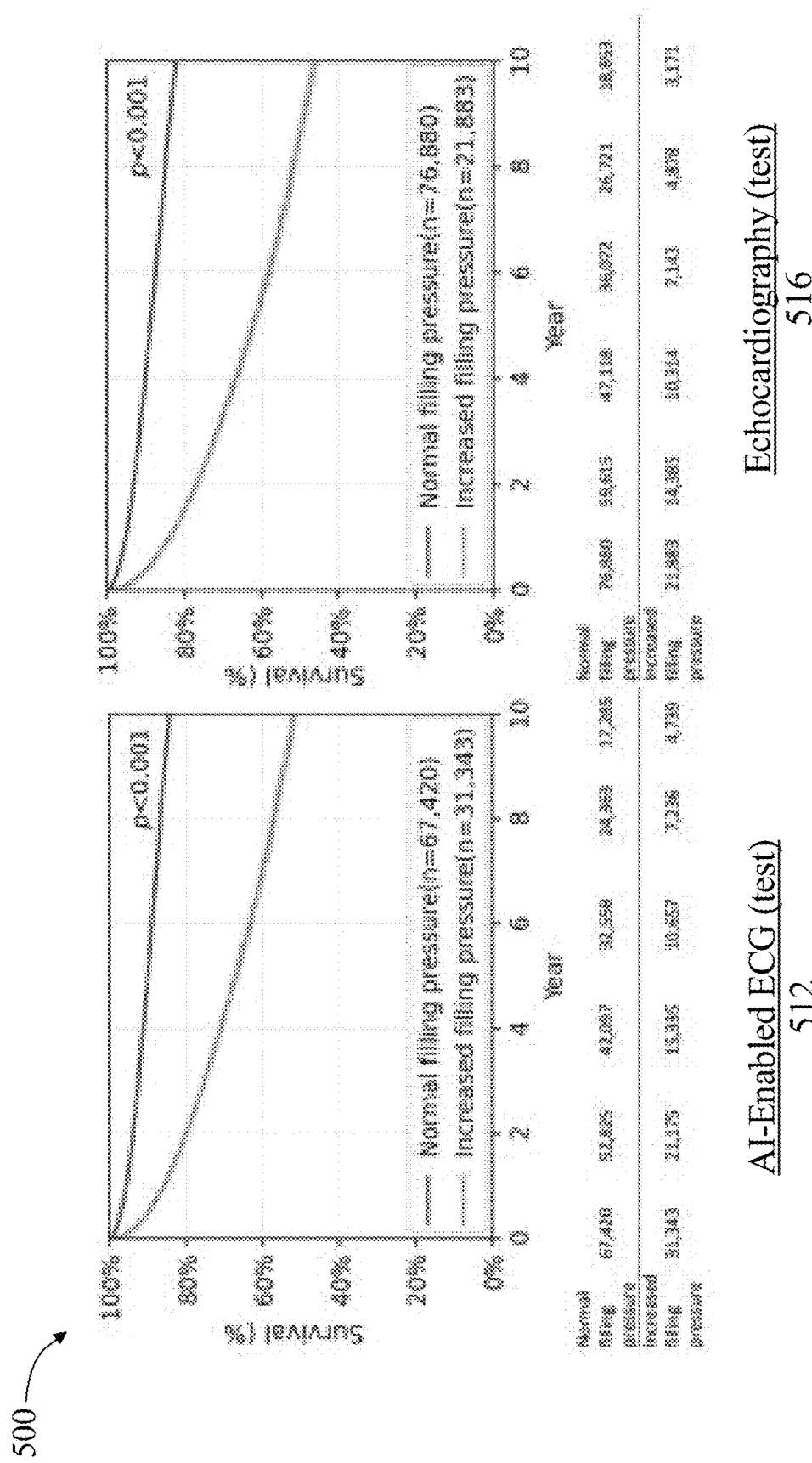
Figure 5D:
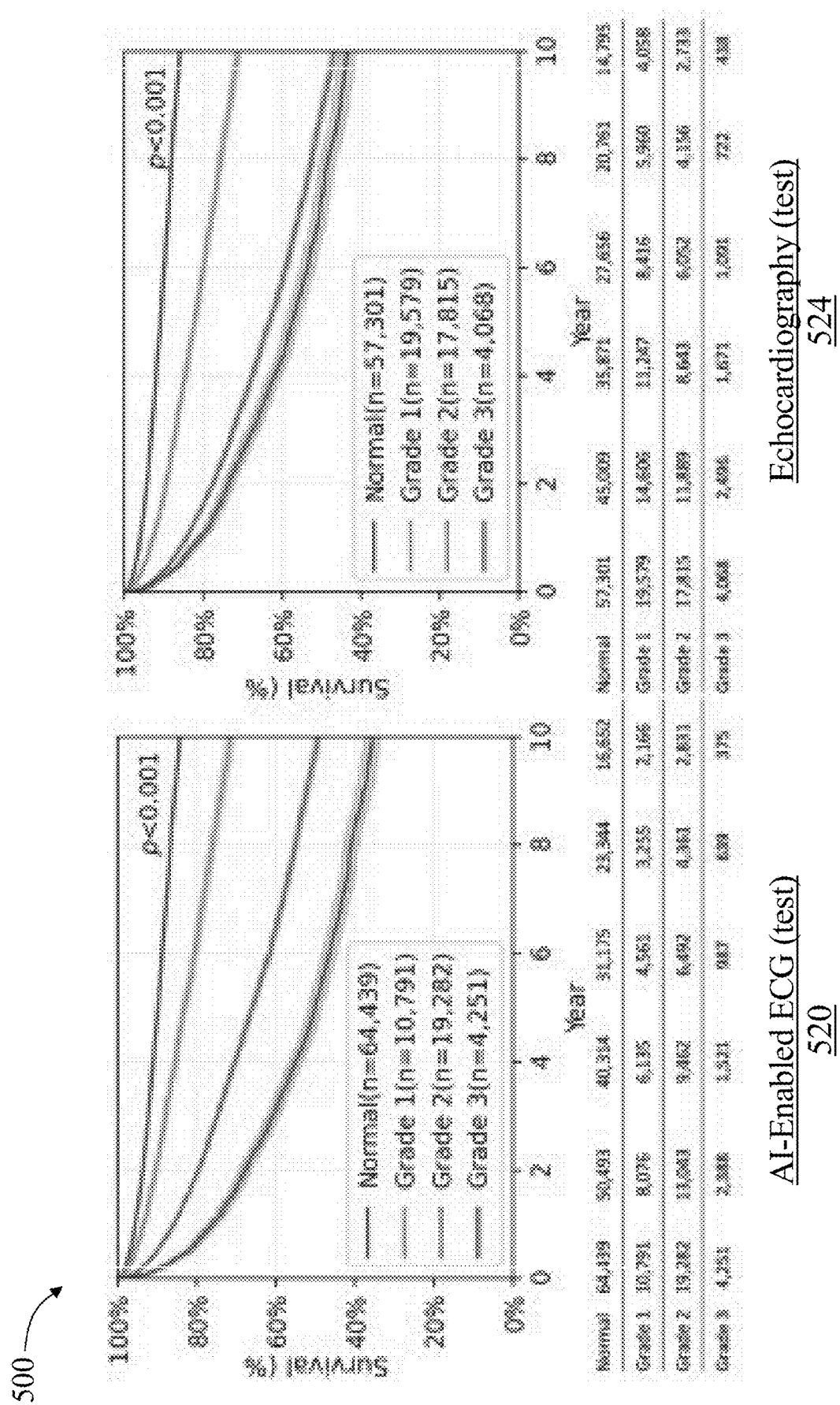
Figure 5E:
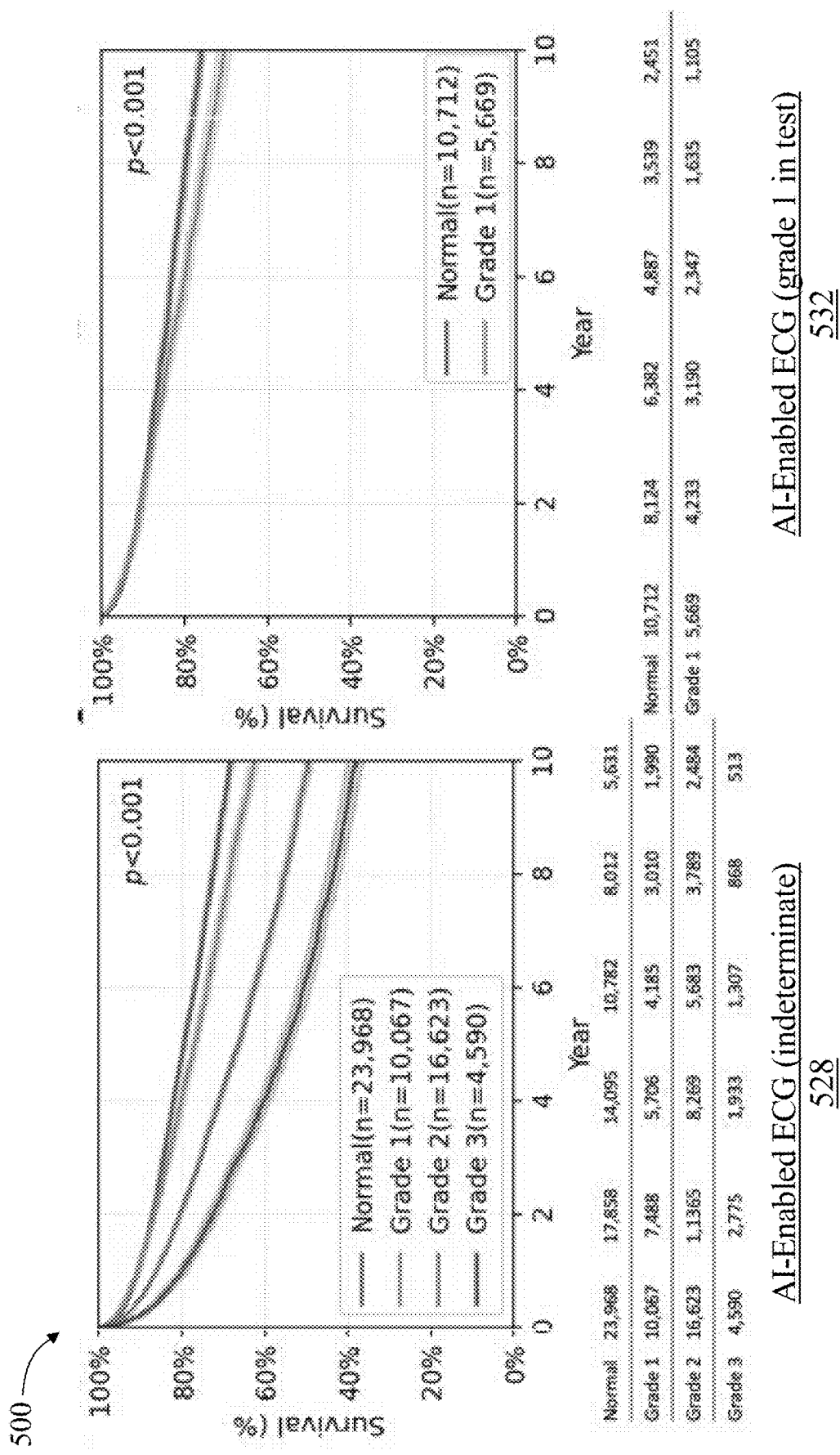

Now referring to FIG. 5C-E, shown are all-cause mortality using a Kaplan-Meier curve with 95% point-wise confidence intervals is illustrated. FIG. 5C illustrates Kaplan-Meier curve for a test group of patients according to filling pressure predicted by the AI-enabled ECG 512 and Kaplan-Meier curve for a test group of patients according to filling pressure by echocardiography 516. FIG. 5D illustrates Kaplan-Meier curve for the test group according to diastolic function grades predicted by the AI-enabled ECG 520 and Kaplan-Meier curve according to diastolic function grades by echocardiography 524. FIG. 5E illustrates Kaplan-Meier curve for the indeterminate group according to diastolic function grades predicted by the deep learning model 528 and Kaplan-Meier curve for echocardiographic grade 1 in the testing group according to diastolic function grade normal and grade 1 predicted by the AI-enabled ECG 532. Log-rank test was used for the p-value.

Figure 5F:
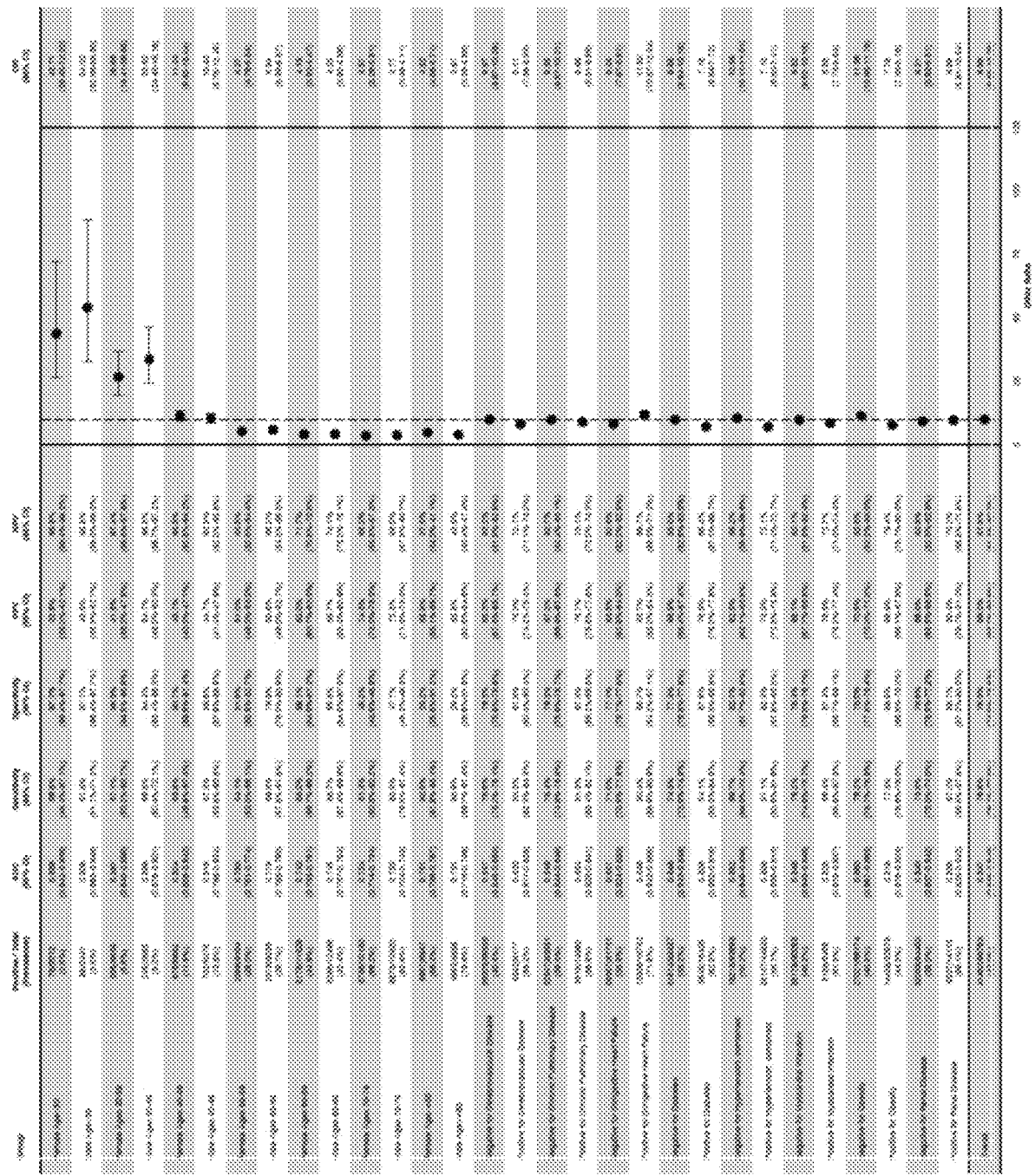

Now referring to FIG. 5F-F3, illustrated is AUC, sensitivity, specificity, PPV, NPV, and odd ratio (OR) with 95% confidence intervals across age, gender, and comorbidity subsets. FIG. 5F specifically depicts grade 1 or above. FIG. 5F2 specifically depicts grade 2 or above (increased filling pressure). Lastly, FIG. 5F3 specifically depicts grade 3.

Figure 5G:
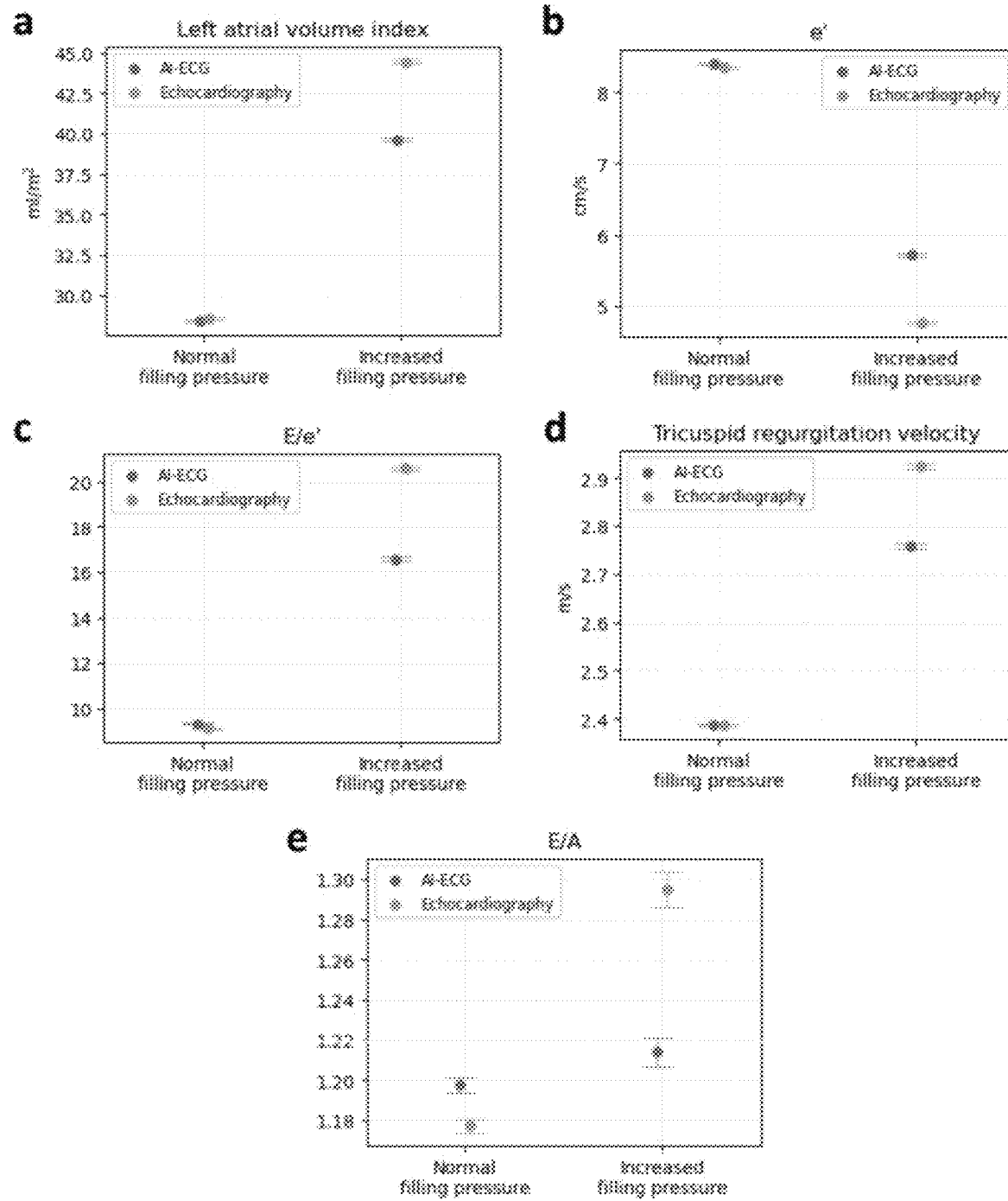

Now referring to FIG. 5G, illustrated is the distribution of left atrial volume index, e', E/e', tricuspid regurgitation velocity, and E/A according to filling pressure by our AI-ECG and echocardiography in test set. Each point represents the mean value with 95% confidence interval. Normal filling pressure includes normal and grade 1, and increased filling pressure includes grade 2 and grade 3.

Figure 5H:
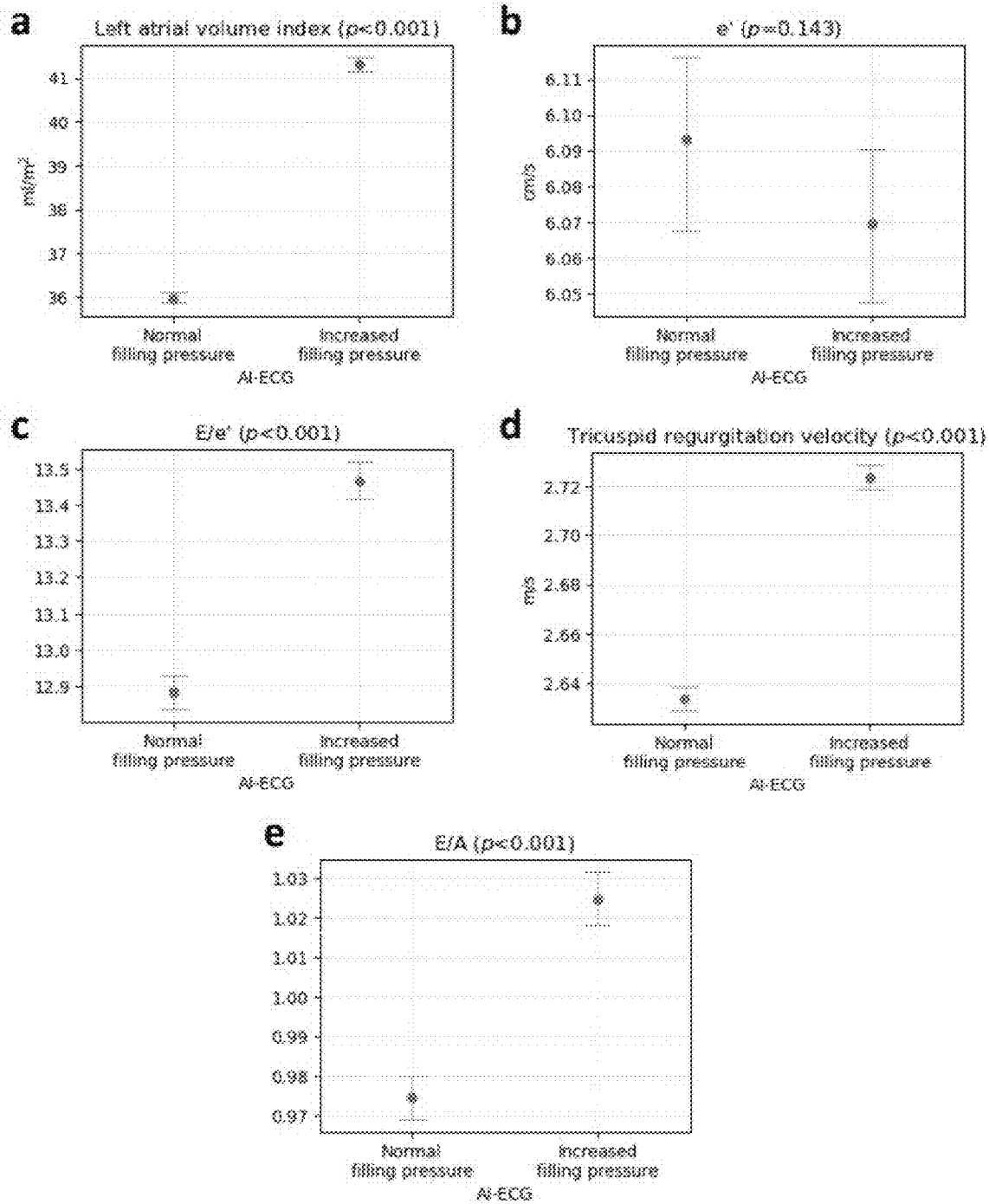

Now referring to FIG. 5H, illustrated is the distribution of left atrial volume index, e', E/e', tricuspid regurgitation velocity, and E/A according to filling pressure by our AI-ECG in indeterminate set. Each point represents the mean value with 95% confidence interval. Normal filling pressure includes normal and grade 1, and increased filling pressure includes grade 2 and grade 3. Student's t-test was used for p-value.

Figure 5I:
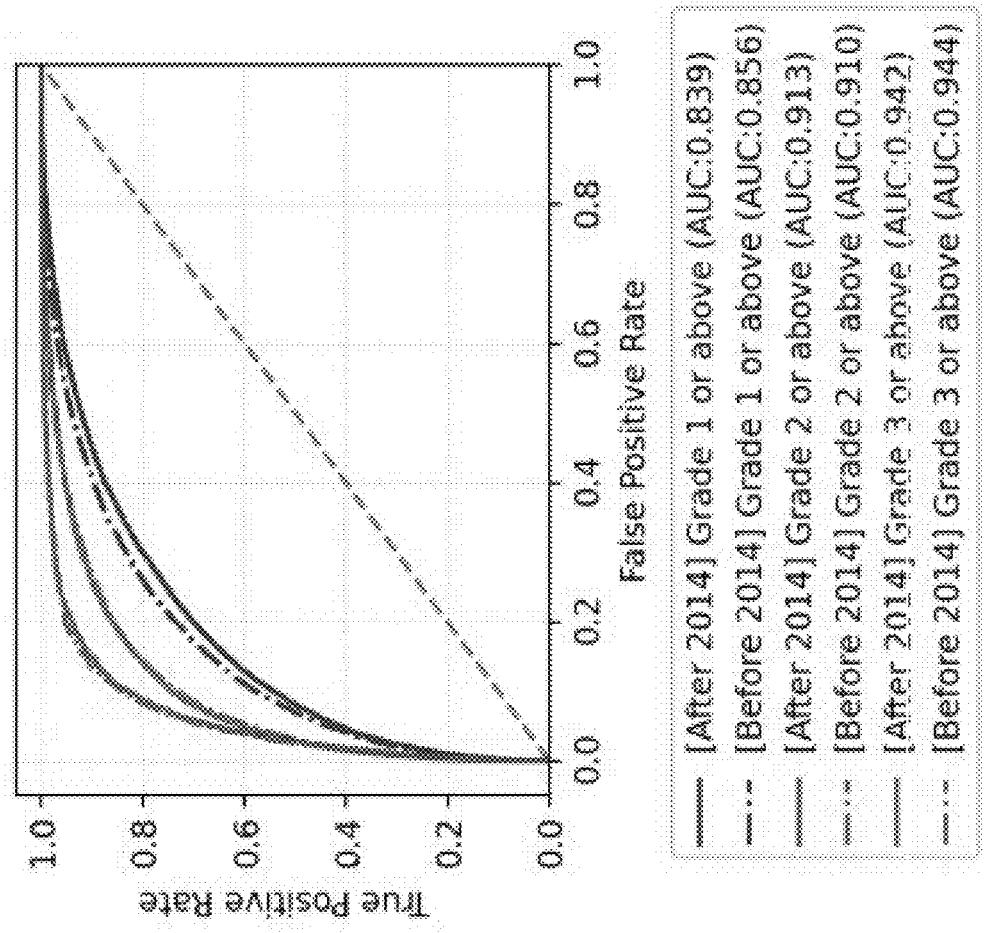

Now referring to FIG. 5I, illustrated is the ROC curves of AI-ECG between, before, and after the median year of the echocardiography exam in the test set. ROC plots for detecting diastolic function grades using ordinal scale.

Figure 5J:
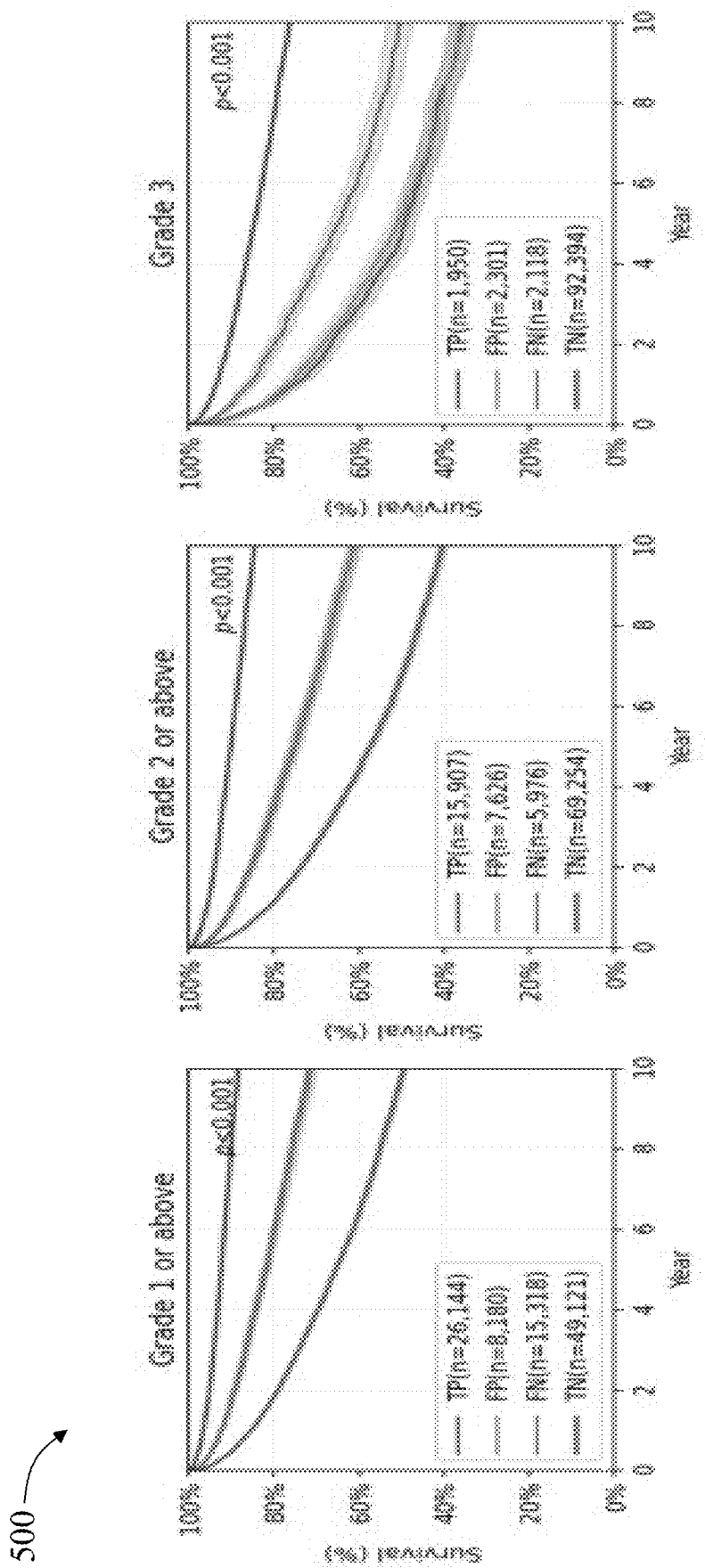

Now referring to FIG. 5J, illustrated is all-cause mortality using a Kaplan-Meier curve with 95% confidence intervals and p-value from a log-rank test by true positive (TP), false positive (FP), false negative (FN), and true negative (TN) for grade 1 or above, grade 2 or above, and grade 3.

Figure 5K:
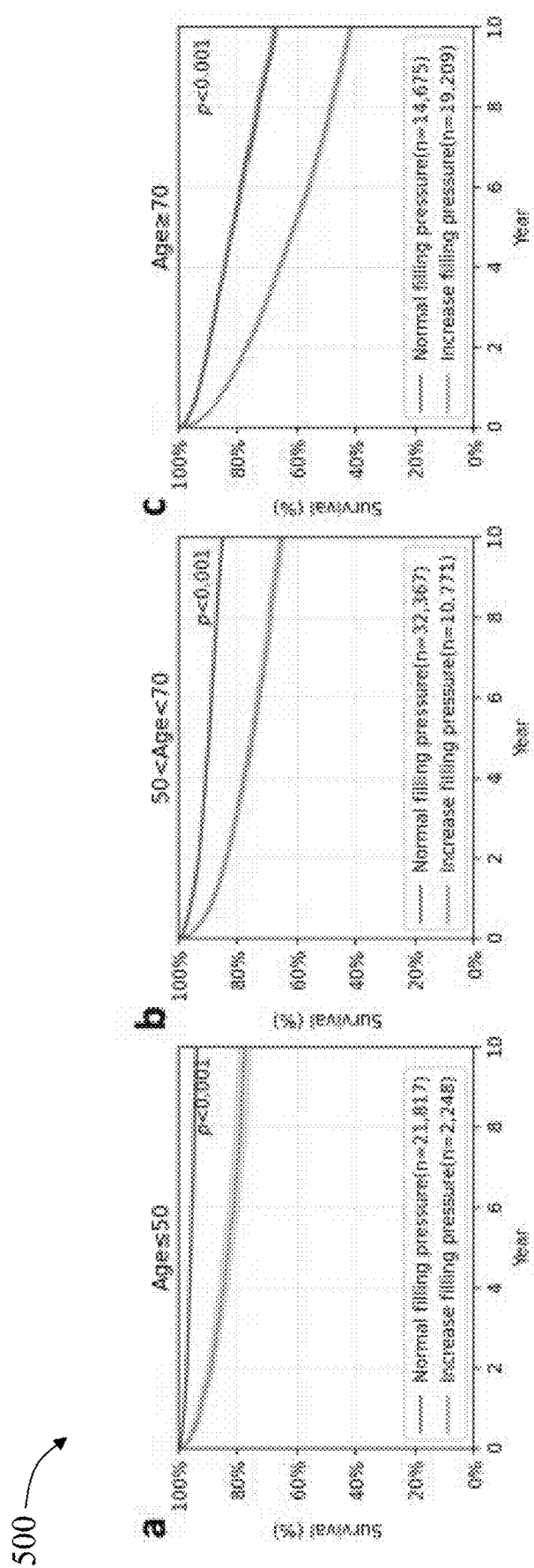

Now referring to FIG. 5K, illustrated is all-cause mortality using a Kaplan-Meier curve with 95% confidence intervals and p-value from a log-rank test by age. FIG. 5M (a) illustrates a Kaplan-Meier curve for test group of patients (age≤50) according to the filling pressure by our AI_ECG (HR 1.413, 95% CI 1.329-1.503). FIG. 5M (b) illustrates a Kaplan-Meier curve for test group of patients (50<age <70) according to the filling pressure by our AI_ECG (HR 1.35, 9% CI 1.313-1.388). FIG. 5M (c) illustrates a Kaplan-Meier curve for test group of patients (age ≥70) according to the filling pressure by our AI_ECG (HR 1.235, 95% CI 1.211-1.26). HRs were calculated with four grades after adjusting by age, sex, and comorbidities.

Figure 5L:
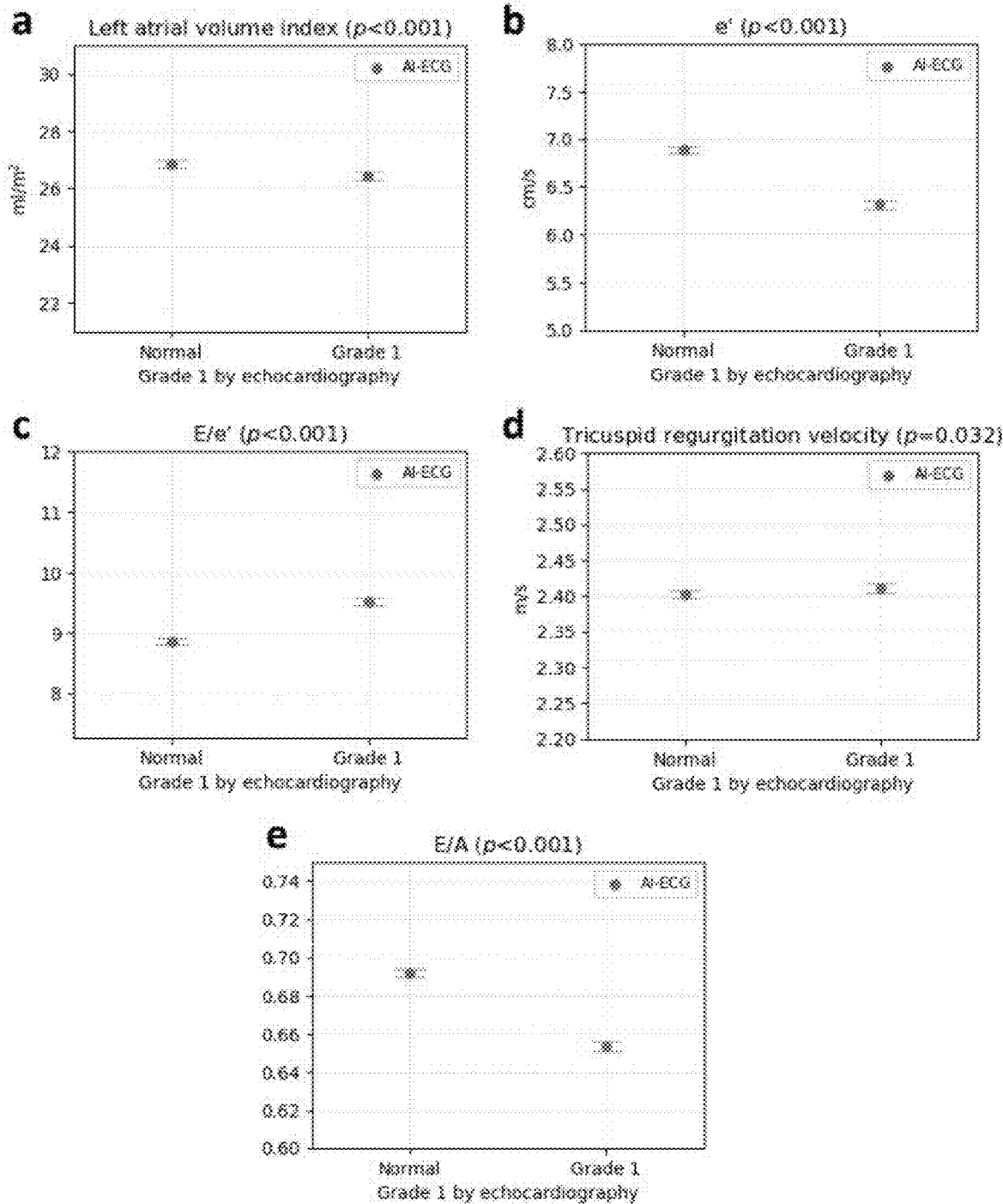
Figure 5M:
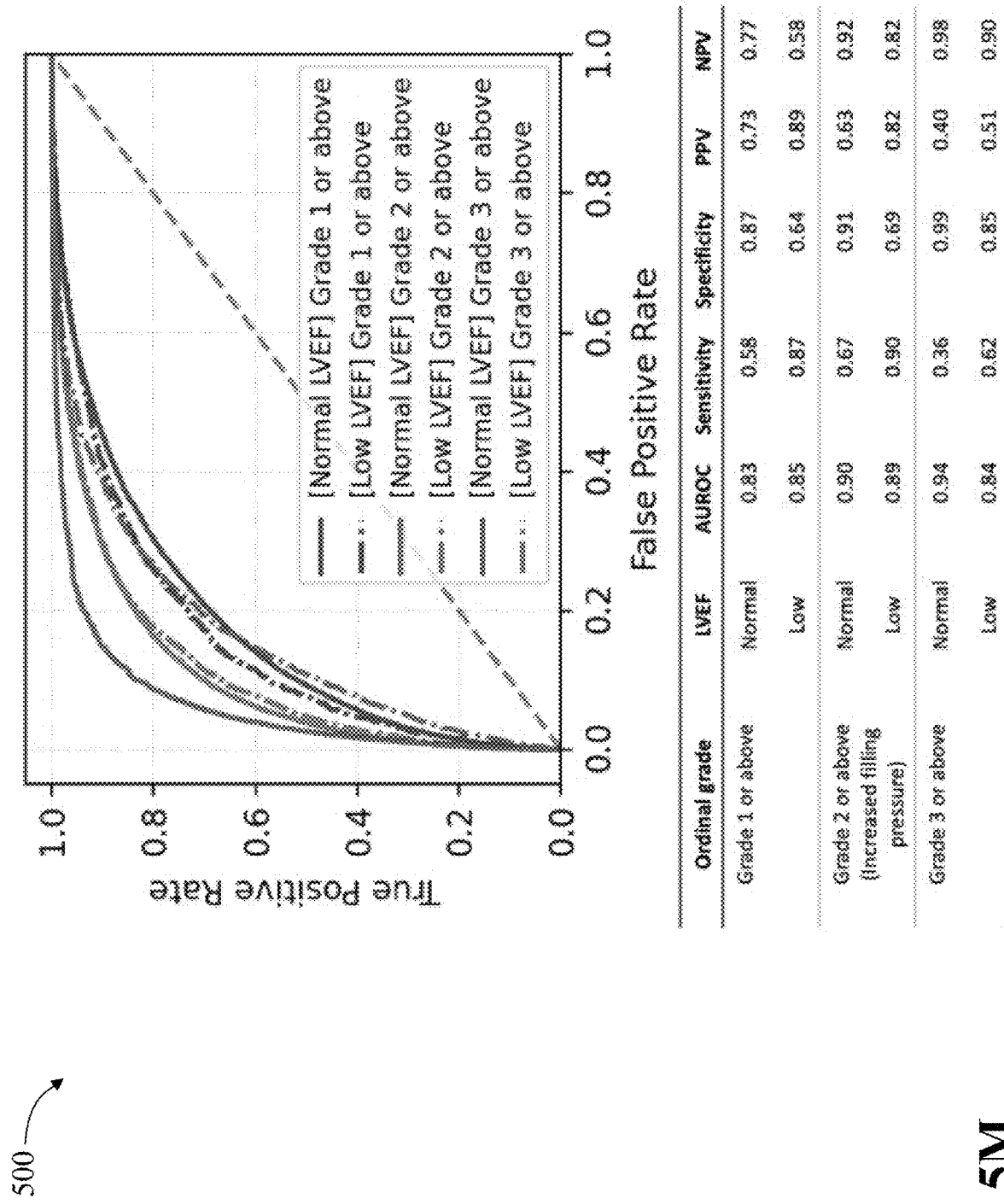

Now referring to FIG. 5L, illustrated is the distribution of left atrial volume index, e', E/e', tricuspid regurgitation velocity, and E/A according to diastolic filling pressure by our AI-ECG in grade 1 by echocardiography. Each point represents the mean value with 95% confidence interval. Normal filling pressure includes normal and grade1, and increased filling pressure includes grade 2 and grade 3. Student's t-test was used for p-value.

Now referring to FIG. 5M, illustrated is the ROC curves and performance of AI-ECG in normal ejection fraction and low ejection fraction, defined as left ventricular ejection fraction.

Figure 5N:
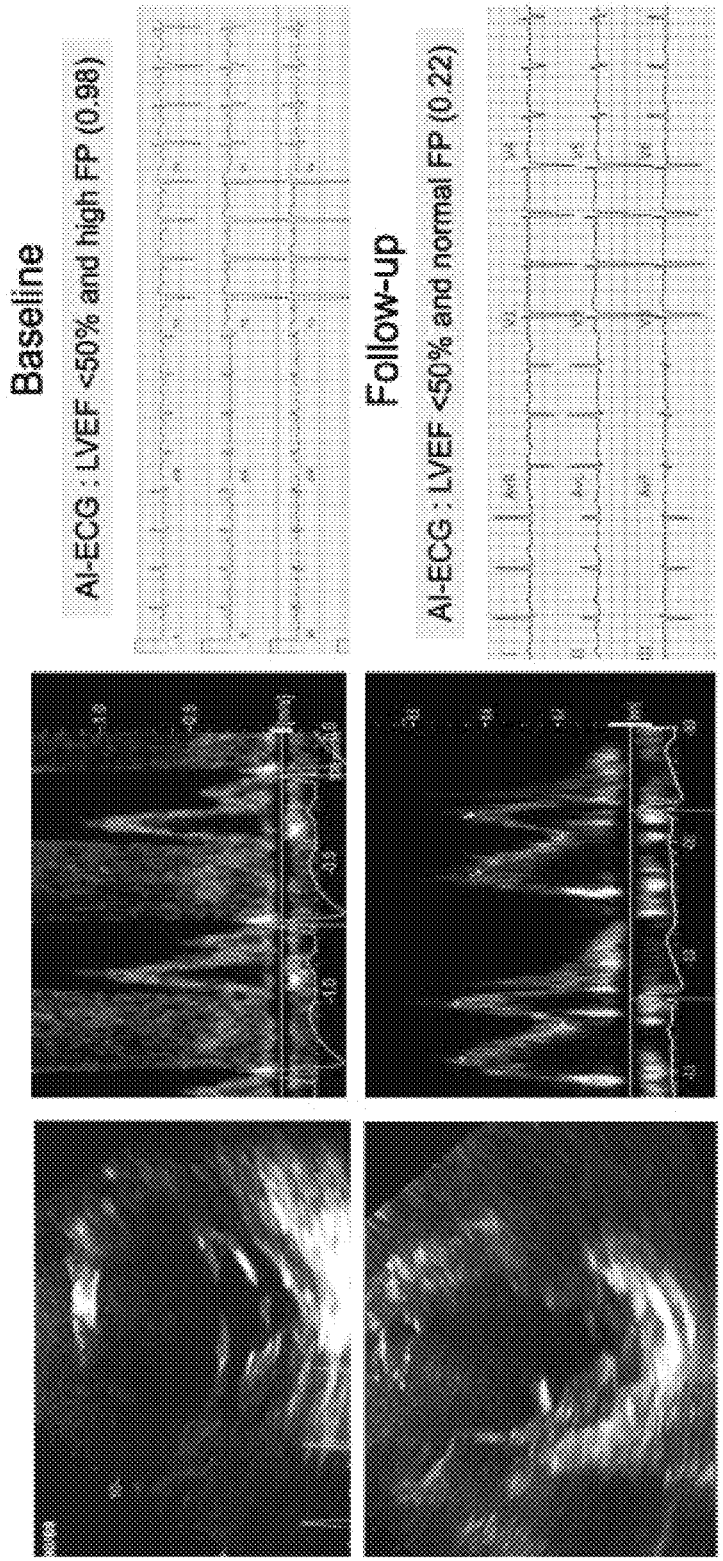

Now referring to FIG. 5N, illustrated is an illustrative case of a heart failure patient present in the exemplary study of the particular implementation.

Figure 5O:
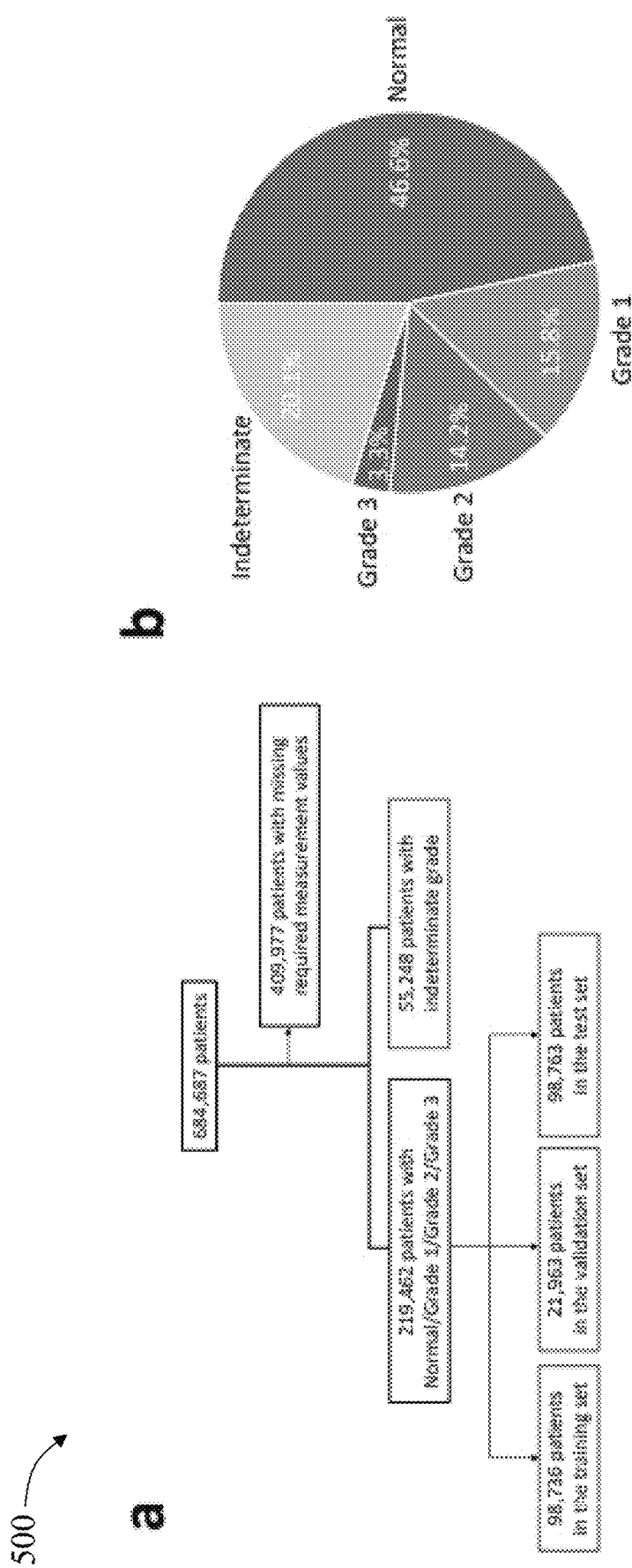

Now referring to FIG. 5O, illustrated is a flow chart of dataset construction and patient distribution. FIG. 5O(a) is a flow chart demonstrating patient selection. FIG. 5O(b) is a pie chart for dataset split.

Figure 5P:
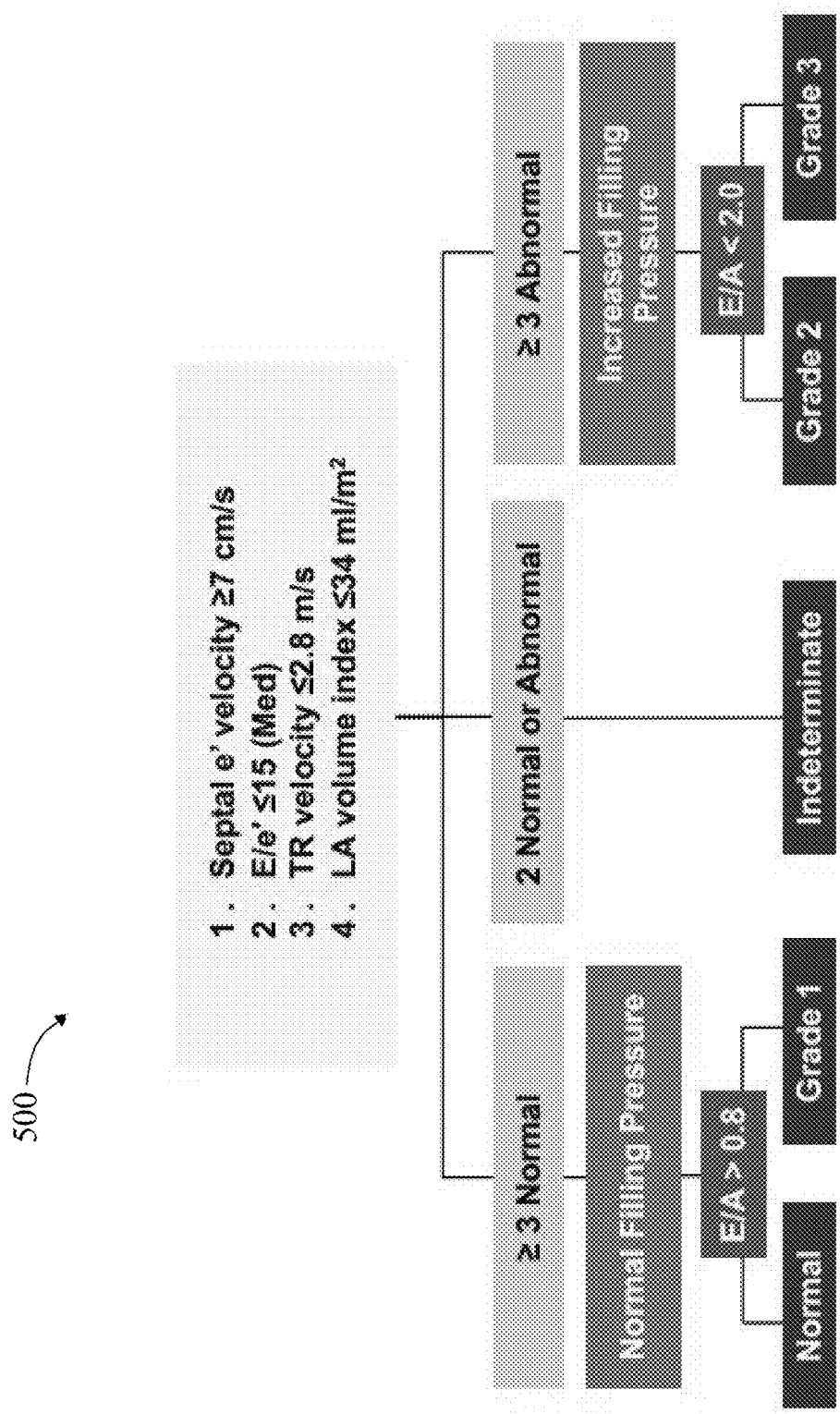

Now referring to FIG. 5P, illustrated is an algorithm for assessment of diastolic filling pressure and function.

DISCUSSION

Continuing to reference FIGS. 5A-P, and the particular implementation of an apparatus for AI-supported diagnostic assessment tool, a deep neural network of an AI-enabled ECG was developed to detect patients with increased filling pressure and to grade diastolic dysfunction. This particular implementation shows three main findings. First, the AI-enabled ECG model may be able to identify patients with increased left ventricular filling pressure with high accuracy. Second, the prediction of the model for diastolic function and filling pressure is well aligned with echocardiographically determined diastolic function and estimated diastolic filling pressure. Additionally, ECG-based diastolic function grading and filling pressure assessment may be associated with mortality. The particular implementation of this model was designed to predict filling pressure as well as diastolic function grade using only an ECG. This is much more cost-effective and scalable for a wider range of the population. It is noteworthy that echocardiographic parameters in patients with different diastolic function grades predicted by the AI-enabled ECG were comparable to those in the corresponding grades determined by echocardiography. Advanced diastolic dysfunction with increased filling pressure determined by echocardiography may predict increased mortality in various cardiovascular disorders including heart failure with preserved ejection fraction (HFpEF). Likewise, the AI-enabled ECG discriminated risk of death as well as the stratification based upon echocardiography may do the same. This may be explained by characteristic ECG features shaped by delayed myocardial relaxation and increased filling pressure detected by the neural network. The model was predictive of mortality based on increased filling pressure. The data suggests a promising role for AI-enabled ECG as a screening test to identify or exclude a cardiac cause in patients who present with dyspnea or other signs of heart failure. HFpEF is a common and growing public health problem that particularly affects older adults. Demonstration of increased left ventricular filling pressure may support the diagnosis of HFpEF, but in most cases may require either echocardiographic or even invasive evaluation. The present AI-enabled ECG may be able to identify patients with a high likelihood of HFpEF in conjunction with AI-ECG determination of left ventricular ejection fraction. It may also be possible to identify relatively asymptomatic patients with early-stage HFpEF. AI-ECG used for diastolic function with a high negative predictive value may exclude cardiac etiology in patients with unexplained dyspnea when the AI-enabled ECG indicates normal diastolic function and/or filling pressure. A preliminary retrospective data in two thousand patients with dyspnea evaluated in the emergency department at our medical center, AI-ECG determination of normal and increased filling pressure was shown to be significantly associated with noncardiac and cardiac dyspnea, respectively. In patients with known heart failure, this model may be able to monitor response to its management to optimize the filling pressure. Since the AI-enabled ECG trained by single-lead or median beat ECG showed a promising performance, it may be incorporated into the patient's watch to adjust heart failure medications. Echocardiography is an established diagnostic tool with well documented reliability in the determination of diastolic function and filling pressure and was used as the reference technique in this study. The present data suggests that the AI-enabled ECG may also offer incremental value to echocardiographic assessment of diastolic function. The model may predict diastolic filling pressure when echocardiography is not able to assess diastolic function, which is a relatively frequent situation in clinical practice. Moreover, the risk of death was robustly predicted by the particular implementation of the model in patients whose diastolic function assessment was indeterminate by echocardiography. Echocardiographic parameters reflecting diastolic function and filling pressure (the ratio between mitral inflow early diastolic velocity (E) and mitral annulus early diastolic velocity (e') (E/e'), left atrial volume index, tricuspid regurgitation velocity, and the ratio between mitral inflow early and late velocity (E/A)) differed between normal and increased filling pressure predicted by ECG in the indeterminate group, similar to those in patients with clear echocardiographic determination of diastolic function. A main reason for indeterminate diastolic grading by echocardiography may be a discrepancy among the four variables used for evaluating diastolic function. The recommended echocardiographic diastolic function parameters' normal values may be specific for diastolic dysfunction/increased filling pressures but may not be sensitive. The difference in echocardiographic diastolic parameters between the increased and normal filling pressure groups was smaller in the indeterminate than in the test group. It is noteworthy that 54.7% of the patients with grade 1 by echocardiography were identified as normal by our AI-enabled ECG. A main difference between normal and grade 1 dysfunction is delayed myocardial relaxation, but both have normal filling pressures. Grade 1 diastolic dysfunction by echocardiography may include a heterogeneous population. This may be a common finding with normal senescence but may also be observed in those with compensated heart failure. Patients predicted as normal by our model were younger (66.1±10.9 vs. 71.6±9.1 years) and had fewer comorbidities compared to patients with grade 1 diastolic dysfunction by AI-ECG and echocardiography (Table 6). Left atrial volume index, e', E/e', and E/A were significantly different (p<0.001) between the two groups. Moreover, the group with grade 1 diastolic dysfunction by echocardiography and normal diastolic function by the present model had lower mortality than the group with grade 1 diastolic dysfunction by both echocardiography and the model. One-third of the patients with grade 1 dysfunction at rest developed increased filling pressure with exercise. The AI-ECG model had no exclusion criteria and the patients with reduced ejection fraction or cardiac diseases that were characterized by both diastolic dysfunction and abnormal ECG patterns such as hypertrophic cardiomyopathy, cardiac amyloidosis, and/or aortic stenosis were included. The majority of the patients with grade 3 diastolic dysfunction by AI-ECG had cardiac amyloidosis or reduced left ventricular ejection fraction followed by moderate to severe mitral regurgitation and hypertrophic cardiomyopathy (Table 7). There were 9072 patients with low ejection fraction in the testing group and 3007 (33%) of them were predicted as having normal diastolic function or grade 1 by AI-ECG, but they had lower NPV compared to that of the patients with normal ejection fraction. Within the study there existed a specific case of a 30-year-old female who developed heart failure due to postpartum cardiomyopathy with LVEF of 30%. AI-ECG at that time showed reduced L VEF and increased filling pressure. She became asymptomatic with heart failure treatment, but L VEF remained reduced. AI-ECG at follow-up showed reduced LVEF and normal LV filling pressure.

TABLE 6

|  | Normal (n = 10,712) | Grade 1 (n = 5,669) | p-value |
|---|---|---|---|
| Age, y | 66.1 ± 10.9 | 71.6 ± 9.1 | <0.001 |
| Female sex, Number (%) | 5,194 (48.5%) | 2,823 (49.8%) | 0.861 |
| Myocardial infarction, Number (%) | 799 (7.5%) | 512 (9.0%) | <0.001 |
| Congestive heart failure, Number (%) | 1,063 (10.0%) | 747 (13.2%) | <0.001 |
| Cerebrovascular disease, Number (%) | 1,064 (10.0%) | 737 (13.0%) | <0.001 |
| Chronic pulmonary disease, Number (%) | 1,608 (15,1%) | 935 (16.5%) | 0.015 |
| Diabetes Mellitus, Number (%) | 1,643 (15.3%) | 1,001 (17.7%) | <0.001 |
| Renal disease, Number (%) | 1,185 (11.1%) | 788 (13.9%) | <0.001 |
| Hypertension, Number (%) | 5,319 (49.8%) | 3,350 (59.1%) | <0.001 |
| Obesity, Number (%) | 3,565 (33.3%) | 2,044 (36.1%) | <0.001 |

TABLE 7

| | Test (n = 98,763) | | | |
|---|---|---|---|---|
| AI-ECG diastolic function grade | Normal (n = 64,439) | Grade 1 (n = 10,791) | Grade 2 (n = 19,282) | Grade 3 (n = 4,251) |
| HCM | 1,103 (1.7%) | 233 (2.2%) | 1,267 (6.6%) | 852 (20%) |
| Amyloidosis | 2,590 (4%) | 373 (3.5%) | 1,571 (8.1%) | 2,225 (52.3%) |
| Moderate to severe MR | 1,070 (1.7%) | 144 (1.3%) | 1,958 (10.2%) | 1,017 (23.9%) |
| Moderate to severe AS | 588 (<1%) | 242 (2.2%) | 1,374 (7.1%) | 265 (6.2%) |
| Reduced LVEF (<50%) | 2,252 (3.5%) | 755 (7%) | 3,813 (19.8%) | 2,252 (53%) |

CONCLUSION

In conclusion, the present study shows that the application of the particular implementation of an apparatus for AI-supported diagnostic assessment tool, namely an AI-enabled ECG allows for grading of diastolic dysfunction and estimation of filling pressure, with a robust prognostic value similar to that of comprehensive echocardiography. These data suggest that AI-enabled ECG may be useful to enhance diagnostic evaluation of disorders associated with diastolic dysfunction and increased filling pressure in the community, including heart failure with preserved ejection fraction.

Figure 6:
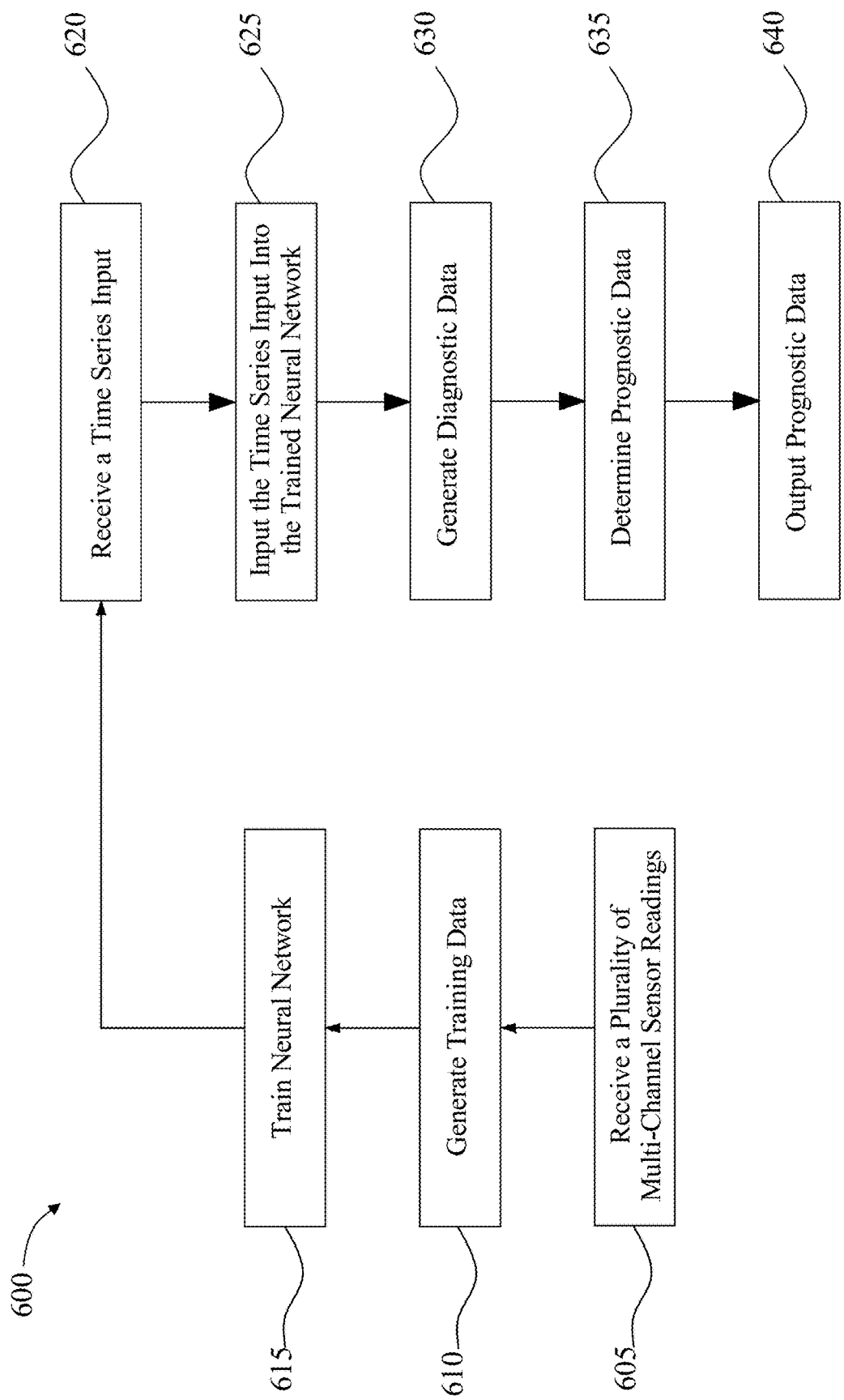
FIG. 6 is a flow diagram illustrating an exemplary method of training an apparatus for artificial intelligence-supported diagnostic assessments.

Now referring to FIG. 6, a flow diagram is illustrated depicting the method of training an apparatus for artificial intelligence-supported diagnostic assessments 600. Method 600 may be implemented and/or altered in any way as described within this disclosure. At step 605, a computing device receives a plurality of multi-channel sensor readings of physiological data; this may be implemented, without limitation, as described above in connection with FIGS. 1-5A-C. At step 610, computing device generates training data correlating each of the plurality of multi-channel sensor readings with a plurality of diagnostic labels; this may be implemented, without limitation, as described above in connection with FIGS. 1-5A-C. At step 615, computing device trains a neural network using the plurality of diagnostic labels; this may be implemented, without limitation, as described above in connection with FIGS. 1-5A-C. At step 620, computing device receives a time series input describing user physiological data from at least a sensor; this may be implemented, without limitation, as described above in connection with FIGS. 1-5A-C. At step 625, computing device inputs time series input into the trained neural network; this may be implemented, without limitation, as described above in connection with FIGS. 1-5A-C. At step 630, computing devices generates diagnostic data as a function of the time series input and the trained neural network; this may be implemented, without limitation, as described above in connection with FIGS. 1-5A-C. At step 635, computing device determines prognostic data as a function of the diagnostic data; this may be implemented, without limitation, as described above in connection with FIGS. 1-5A-C. At step 640, computing device outputs the prognostic data; this may be implemented, without limitation, as described above in connection with FIGS. 1-5A-C.

It is to be noted that any one or more of the aspects and embodiments described herein may be conveniently implemented using one or more machines (e.g., one or more computing devices that are utilized as a user computing device for an electronic document, one or more server devices, such as a document server, etc.) programmed according to the teachings of the present specification, as will be apparent to those of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of a computing device include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device may include and/or be included in a kiosk.

Figure 7:
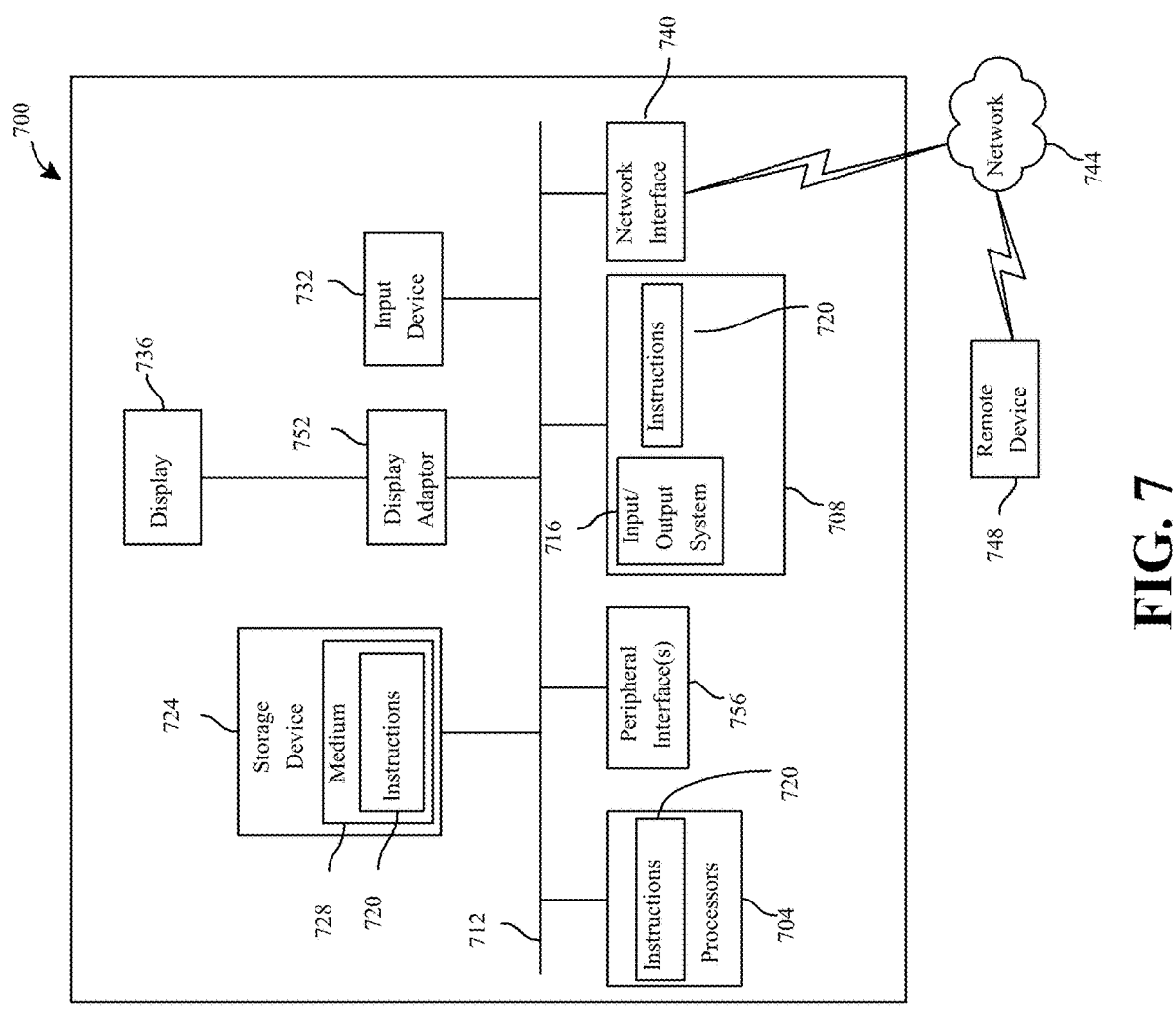
FIG. 7 is a block diagram of a computing system that can be used to implement any one or more of the methodologies disclosed herein and any one or more portions thereof.

FIG. 7 shows a diagrammatic representation of one embodiment of a computing device in the exemplary form of a computer system 700 within which a set of instructions for causing a control system to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computer system 700 includes a processor 704 and a memory 708 that communicate with each other, and with other components, via a bus 712. Bus 712 may include any of several types of bus structures including, but not limited to, a memory bus, a memory controller, a peripheral bus, a local bus, and any combinations thereof, using any of a variety of bus architectures.

Processor 704 may include any suitable processor, such as without limitation a processor incorporating logical circuitry for performing arithmetic and logical operations, such as an arithmetic and logic unit (ALU), which may be regulated with a state machine and directed by operational inputs from memory and/or sensors; processor 704 may be organized according to Von Neumann and/or Harvard architecture as a non-limiting example. Processor 704 may include, incorporate, and/or be incorporated in, without limitation, a microcontroller, microprocessor, digital signal processor (DSP), Field Programmable Gate Array (FPGA), Complex Programmable Logic Device (CPLD), Graphical Processing Unit (GPU), general purpose GPU, Tensor Processing Unit (TPU), analog or mixed signal processor, Trusted Platform Module (TPM), a floating point unit (FPU), system on module (SOM), and/or system on a chip (SoC).

Memory 708 may include various components (e.g., machine-readable media) including, but not limited to, a random-access memory component, a read only component, and any combinations thereof. In one example, a basic input/output system 716 (BIOS), including basic routines that help to transfer information between elements within computer system 700, such as during start-up, may be stored in memory 708. Memory 708 may also include (e.g., stored on one or more machine-readable media) instructions (e.g., software) 720 embodying any one or more of the aspects and/or methodologies of the present disclosure. In another example, memory 708 may further include any number of program modules including, but not limited to, an operating system, one or more application programs, other program modules, program data, and any combinations thereof.

Computer system 700 may also include a storage device 724. Examples of a storage device (e.g., storage device 724) include, but are not limited to, a hard disk drive, a magnetic disk drive, an optical disc drive in combination with an optical medium, a solid-state memory device, and any combinations thereof. Storage device 724 may be connected to bus 712 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 724 (or one or more components thereof) may be removably interfaced with computer system 700 (e.g., via an external port connector (not shown)). Particularly, storage device 724 and an associated machine-readable medium 728 may provide nonvolatile and/or volatile storage of machine-readable instructions, data structures, program modules, and/or other data for computer system 700. In one example, software 720 may reside, completely or partially, within machine-readable medium 728. In another example, software 720 may reside, completely or partially, within processor 704.

Computer system 700 may also include an input device 732. In one example, a user of computer system 700 may enter commands and/or other information into computer system 700 via input device 732. Examples of an input device 732 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device 732 may be interfaced to bus 712 via any of a variety of interfaces (not shown) including, but not limited to, a serial interface, a parallel interface, a game port, a USB interface, a FIRE-WIRE interface, a direct interface to bus 712, and any combinations thereof. Input device 732 may include a touch screen interface that may be a part of or separate from display 736, discussed further below. Input device 732 may be utilized as a user selection device for selecting one or more graphical representations in a graphical interface as described above.

A user may also input commands and/or other information to computer system 700 via storage device 724 (e.g., a removable disk drive, a flash drive, etc.) and/or network interface device 740. A network interface device, such as network interface device 740, may be utilized for connecting computer system 700 to one or more of a variety of networks, such as network 744, and one or more remote devices 748 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 744, may employ a wired and/or a wireless mode of communication. In general, any network topology may be used. Information (e.g., data, software 720, etc.) may be communicated to and/or from computer system 700 via network interface device 740.

Computer system 700 may further include a video display adapter 752 for communicating a displayable image to a display device, such as display device 736. Examples of a display device include, but are not limited to, a liquid crystal display (LCD), a cathode ray tube (CRT), a plasma display, a light emitting diode (LED) display, and any combinations thereof. Display adapter 752 and display device 736 may be utilized in combination with processor 704 to provide graphical representations of aspects of the present disclosure. In addition to a display device, computer system 700 may include one or more other peripheral output devices including, but not limited to, an audio speaker, a printer, and any combinations thereof. Such peripheral output devices may be connected to bus 712 via a peripheral interface 756. Examples of a peripheral interface include, but are not limited to, a serial port, a USB connection, a FIREWIRE connection, a parallel connection, and any combinations thereof.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve methods, systems, and software according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:

1. An apparatus for artificial intelligence-supported diagnostic assessment, wherein the apparatus comprises: a sensor for sensing a time series input;
   at least a processor, wherein the processor is configured to:
   receive a plurality of multi-channel sensor readings of physiological data;
   generate training data correlating each of the plurality of multi-channel sensor readings with a plurality of diagnostic labels;
   train a neural network using the plurality of diagnostic labels;
   update the training data as a function of new training examples;
   retrain the neural network as a function of the updated training data, wherein the retraining occurs when a preconfigured threshold of new training examples is exceeded;
   receive the time series input describing user physiological data from at least the sensor;
   input the time series input into the trained neural network;
   generate diagnostic data as a function of the time series input and the trained neural network, wherein the diagnostic data includes a classification under a plurality of groups, wherein the groups are comprised of:
   normal LV function;
   LVSD only;
   LVDD only; and
   both LVSD and LVDD;

determine prognostic data as a function of the diagnostic data; and output the prognostic data; and a display device, wherein the output of the prognostic data is displayed on the display device.

2. The apparatus of claim 1, wherein the time series input is comprised of electrocardiogram (ECG) data.

3. The apparatus of claim 2, wherein the plurality of multi-channel sensor readings further comprises a plurality of ECG readings, and the plurality of training data further comprises the plurality of ECG readings, and generating the plurality of training data further comprises:

receiving echocardiogram data correlated to each ECG reading of the plurality of ECG readings; and generating the plurality of diagnostic labels using the echocardiogram data.

4. The apparatus of claim 1, wherein the neural network is a multi-output convolutional neural network.

5. The apparatus of claim 1, wherein the neural network is trained using general-use lead data, wherein the general-use lead data refers to the lead data used for a diagnostic tool.

6. The apparatus of claim 1, wherein the neural network is trained using reduced general-use lead data, wherein the reduced general-use lead data refers to a reduction in the leads used in acquiring the lead data.

7. The apparatus of claim 1, wherein the neural network is trained as a function of lead data gathered from 12-lead ECGs performed within 14 days of transthoracic echocardiography, wherein the plurality of multi-channel sensor readings of physiological data are comprised of the 12-lead ECG data and the lead data correlated to each 12-lead ECG datum.

8. The apparatus of claim 1, wherein the diagnostic data includes an assessment of the LVDD.

9. A method for training an artificial intelligence-supported diagnostic assessment tool, wherein the method comprises: sensing a time series input via a sensor;

receiving a plurality of multi-channel sensor readings of physiological data;

generating training data correlating each of the plurality of multi-channel sensor readings with a plurality of diagnostic labels;

training a neural network using the plurality of diagnostic labels;

updating the training data as a function of new training examples;

retraining the neural network as a function of the updated training data, wherein the retraining occurs when a preconfigured threshold of new training examples is exceeded;

receiving the time series input describing user physiological data from at least the sensor;

inputting the time series input into the trained neural network;

generating diagnostic data as a function of the time series input and the trained neural network, wherein the diagnostic data includes a classification under a plurality of groups, wherein the groups are comprised of:
normal LV function;
LVSD only;
LVDD only; and
both LVSD and LVDD;

determining prognostic data as a function of the diagnostic data; and outputting the prognostic data; and displaying the output of the prognostic data on a display device.

10. The method of claim 9, wherein the time series input is comprised of electrocardiogram (ECG) data.

11. The method of claim 10, wherein the plurality of multi-channel sensor readings further comprises a plurality of ECG readings, and the plurality of training data further comprises the plurality of ECG readings, and generating the plurality of training data further comprises:

receiving echocardiogram data correlated to each ECG reading of the plurality of ECG readings; and generating the plurality of diagnostic labels using the echocardiogram data.

12. The method of claim 9, wherein the neural network is a multi-output convolutional neural network.

13. The method of claim 9, wherein the neural network is trained using general-use lead data, wherein the general-use lead data refers to the lead data used for a diagnostic tool.

14. The method of claim 9, wherein the neural network is trained using reduced general-use lead data, wherein the reduced general-use lead data refers to a reduction in the leads used in acquiring the lead data.

15. The method of claim 9, wherein the neural network is trained using lead data gathered from 12-lead ECGs performed within 14 days of transthoracic echocardiography, wherein the plurality of multi-channel sensor readings of physiological data are comprised of the 12-lead ECG data and the lead data correlated to each 12-lead ECG datum.

16. The method of claim 9, wherein the diagnostic data includes an assessment of both the LVSD and the LVDD.

\* \* \* \* \*